US012624103B2

(12) United States Patent
Bresson et al.

(10) Patent No.: US 12,624,103 B2
(45) Date of Patent: May 12, 2026

(54) ENGINEERED ANTIBODIES THAT BIND LAG3

(71) Applicant: Yuhan Corporation, Seoul (KR)

(72) Inventors: Damien Bresson, San Diego, CA (US);
Min Soo Kim, San Diego, CA (US);
Heyue Zhou, San Diego, CA (US);
John Dixon Gray, San Diego, CA
(US); Barbara A. Swanson, Encinitas,
CA (US); Alok Singh, San Diego, CA
(US); Lisa Diane Kerwin, San Diego,
CA (US)

(73) Assignee: Yuhan Corporation, Seoul (KR)

( * ) Notice: Subject to any disclaimer, the term of this
patent is extended or adjusted under 35
U.S.C. 154(b) by 752 days.

(21) Appl. No.: 17/915,437

(22) PCT Filed: Apr. 1, 2021

(86) PCT No.: PCT/US2021/025423
§ 371 (c)(1),
(2) Date: Sep. 28, 2022

(87) PCT Pub. No.: WO2021/202904
PCT Pub. Date: Oct. 7, 2021

(65) Prior Publication Data
US 2023/0147852 A1     May 11, 2023

Related U.S. Application Data

(60) Provisional application No. 63/004,798, filed on Apr.
3, 2020.

(51) Int. Cl.
*C07K 16/28* (2006.01)
*A61P 35/00* (2006.01)

(52) U.S. Cl.
CPC .......... *C07K 16/2803* (2013.01); *A61P 35/00*
(2018.01); *C07K 2317/21* (2013.01); *C07K
2317/33* (2013.01); *C07K 2317/565* (2013.01);
*C07K 2317/622* (2013.01); *C07K 2317/92*
(2013.01)

(58) Field of Classification Search
None
See application file for complete search history.

(56) References Cited

U.S. PATENT DOCUMENTS

| | | | |
|---|---|---|---|
| 2011/0189082 A1 | 8/2011 | Kirchner et al. | |
| 2017/0022273 A1* | 1/2017 | Zhou ................. | C07K 16/3023 |
| 2019/0002538 A1 | 1/2019 | Corti | |
| 2019/0153112 A1 | 5/2019 | Triebel et al. | |
| 2019/0169294 A1 | 6/2019 | Konnai et al. | |
| 2021/0147536 A1 | 5/2021 | Wang et al. | |

FOREIGN PATENT DOCUMENTS

| | | |
|---|---|---|
| CA | 3038020 A1 | 3/2018 |
| CN | 110343179 A | 10/2019 |
| JP | 2012-500006 A | 1/2012 |
| WO | 2010/019570 A2 | 2/2010 |
| WO | 2017/015560 A2 | 1/2017 |
| WO | 2019165982 A1 | 9/2019 |
| WO | 2019179365 A1 | 9/2019 |
| WO | 2019192432 A1 | 10/2019 |

OTHER PUBLICATIONS

Partial Supplementary European Search Report dated Sep. 24, 2024
in application No. 21782299.8.
Baixeras et al., "Characterization of the lymphocyte activation gene
3-encoded protein. A new ligand for human leukocyte antigen class
II antigens," J Exp Med. 1992;176:327-337.
Casati et al., "Soluble Human LAG-3 Molecule Amplifies the In
vitro Generation of Type 1 Tumor-Specific Immunity," (2006)
Cancer Res. 66:4450-4460.
El Mir et al., "A Soluble Lymphocyte Activation Gene-3 Molecule
Used as a Vaccine Adjuvant Elicits Greater Humoral and Cellular
Immune Responses to Both Particulate and Soluble Antigens,"
(2000) J. Immunol. 164:5583-5589.
Huang, C. et al., "Role of LAG-3 in Regulatory T Cells," (2004)
Immunity 21:503-513.
Huard et al., "Lymphocyte-activation gene 3/major histocompat-
ibility complex class II interaction modulates the antigenic response
of CD4+ T lymphocytes," (1994) Eur. J. Immunol. 24:3216-3221.
Huard et al., "T cell major histocompatibility complex class II
molecules down-regulate CD4+ T cell clone responses following
LAG-3 binding," (1996) Eur. J. Immunol. 26:1180-1186.
International Search Report corresponding to International Patent
Application No. PCT/US2021/025423, mailed Jul. 19, 2021, 10
pages.
Iouzalen et al., "LAP, a lymphocyte activation gene-3 (LAG-3)-
associated protein that binds to a repeated EP motif in the intracel-
lular region of LAG-3, may participate in the down-regulation of the
CD3/TCR activation pathway," (2001) Eur. J. Immunol. 31:2885-
2891.
Prigent et al., "Lymphocyte activation gene-3 induces tumor regres-
sion and antitumor immune responses," (1999) Eur. J. Immunol.
29:3867-3876.
Triebel et al., "LAG-3, a novel lymphocyte activation gene closely
related to CD4," (1990) J. Exp. Med. 171:1393-1405.
Triebel, "LAG-3: a regulator of T-cell and DC responses and its use
in therapeutic vaccination," (2003) Trends Immunol. 24:619-622.
Workman et al., "Negative regulation of T cell homeostasis by
lymphocyte activation gene-3 (CD223)," (2005) J. Immunol. 174:688-
695.

* cited by examiner

*Primary Examiner* — Julie Wu
(74) *Attorney, Agent, or Firm* — Sughrue Mion, PLLC

(57)     ABSTRACT

The present disclosure provides fully human anti-LAG3 IgG
class antibodies engineered to have amino acid sequence in
their heavy chain variable region and/or light chain variable
region to improve antigen binding, cell binding, T cell
activation and cytokine release capabilities.

16 Claims, 12 Drawing Sheets
Specification includes a Sequence Listing.

Human LAG3 polypeptide:  SEQ ID NO:1
MWEAQFLGLLFLQPLWVAPVKPLQPGAEVPVVWAQEGAPAQLPCSPTIPLQDLSLLRRAG
VTWQHQPDSGPPAAAPGHPLAPGPHPAAPSSWGPRPRRYTVLSVGPGGLRSGRLPLQPRV
QLDERGRQRGDFSLWLRPARRADAGEYRAAVHLRDRALSCRLRLRLGQASMTASPPGSLR
ASDWVILNCSFSRPDRPASVHWFRNRGQGRVPVRESPHHHLAESFLFLPQVSPMDSGPWG
CILTYRDGFNVSIMYNLTVLGLEPPTPLTVYAGAGSRVGLPCRLPAGVGTRSFLTAKWTP
PGGGPDLLVTGDNGDFTLRLEDVSQAQAGTYTCHIHLQEQQLNATVTLAIITVTPKSFGS
PGSLGKLLCEVTPVSGQERFVWSSLDTPSQRSFSGPWLEAQEAQLLSQPWQCQLYQGERL
LGAAVYFTELSSPGAQRSGRAPGALPAGHLLLFLILGVLSLLLLVTGAFGFHLWRRQWRP
RRFSALEQGIHPPQAQSKIEELEQEPEPEPEPEPEPEPEPEPEQL

Cynomolgus monkey LAG3 polypeptide:  SEQ ID NO:2
MWEAQFLGLLFLQPLWVAPVKPPQPGAEISWWAQEGAPAQLPCSPTIPLQDLSLLRRAGV
TWQHQPDSGPPAXAPGHPPVPGHRPAAPYSWGPRPRRYTVLSVGPGGLRSGRLPLQPRVQ
LDERGRQRGDFSLWLRPARRADAGEYRATVHLRDRALSCRLRLRVGQASMTASPPGSLRT
SDWVILNCSFSRPDRPASVHWFRSRGQGRVPVQGSPHHHLAESFLFLPHVGPMDSGLWGC
ILTYRDGFNVSIMYNLTVLGLEPATPLTVYAGAGSRVELPCRLPPAVGTQSFLTAKWAPP
GGGPDLLVAGDNGDFTLRLEDVSQAQAGTYICHIRLQGQQLNATVTLAIITVTPKSFGSP
GSLGKLLCEVTPASGQEHFVWSPLNTPSQRSFSGPWLEAQEAQLLSQPWQCQLHQGERLL
GAAVYFTELSSPGAQRSGRAPGALRAGHLPLFLILGVLFLLLLVTGAFGFHLWRRQWRPR
RFSALEQGIHPPQAQSKIEELEQEPELEPEPELERELGPEPEPGPEPEPEQL

Mouse LAG3 polypeptide:  SEQ ID NO:3
MREDLLLGFLLLGLLWEAPVVSSGPGKELPVVWAQEGAPVHLPCSLKSPNLDPNFLRRGG
VIWQHQPDSGQPTPIPALDLHQGMPSPRQPAPGRYTVLSVAPGGLRSGRQPLHPHVQLEE
RGLQRGDFSLWLRPALRTDAGEYHATVRLPNRALSCSLRLRVGQASMIASPSGVLKLSDW
VLLNCSFSRPDRPVSVHWFQGQNRVPVYNSPRHFLAETFLLLPQVSPLDSGTWGCVLTYR
DGFNVSITYNLKVLGLEPVAPLTVYAAEGSRVELPCHLPPGVGTPSLLIAKWTPPGGGPE
LPVAGKSGNFTLHLEAVGLAQAGTYTCSIHLQGQQLNATVTLAVITVTPKSFGLPGSRGK
LLCEVTPASGKERFVWRPLNNLSRSCPGPVLEIQEARLLAERWQCQLYEGQRLLGATVYA
AESSSGAHSARRISGDLKGGHLVLVLILGALSLFLLVAGAFGFHWWRKQLLLRRFSALEH
GIQPFPAQRKIEELERELETEMGQEPEPEPEPQLEPEPRQL

FIG. 1

Anti-LAG3 antibody 1C5-3A6:  Heavy chain variable region:  SEQ ID NO:4
QVQLVQSGAEVKKPGASVKVSCKASGYTLTDYYIHWVRQAPGQGLEWVGWINPNSGGTNYEQKF
QGRVTMTWDTSISTAYMELSRLTSDDTAVYYCAREGWSNDWYVGYYFDYWGQGTLVTVSS

Anti-LAG3 antibody 1C5-3A6:  Light chain variable region:  SEQ ID NO:5
DIQMTQSPLSLSASVGDRVSITCRASQYIGTSLNWYEQKPGNSPKLLITGASRLQSGVPSRFSG
SGSGTDFTLTINTLQPDDLATYYCHQSYDDPPTFGQGTKLEIK

Anti-LAG3 antibody 2D12-2E3-N102D:  Heavy chain variable region:  SEQ ID NO:6
EVQLVESGGGLVQPGRSLRLSCVASGDGMSDYDMHWVRQAPGKGLEWVSGIGWNSGTIDYADSV
KGRFIISRDNAKNSLYLQMNSLRPEDTALYYCAKEILDYSWMSVYGMDVWGQGTTVTVSS

Anti-LAG3 antibody 2D12-2E3-N102D:  Light chain variable region:  SEQ ID NO:7
DIQMTQSPSSLSASVGDRVTITCRASQNIGTYLNWYQQSPGKAPKLLIYGASSLHSGVPSRVSG
SGSGTDFTLTINTLQPEDFATYFCQQSYNTPPTFGQGTKVEIK

Anti-LAG3 antibody 5C8:  Heavy chain variable region:  SEQ ID NO:8
QVQLVQSGAEVKKPGASVKVSCKASGYTFTSYGISWVRQAPGQGLEWMGWISAYNGNTNYAQKL
QGRVTMTTDTSTSTAYMELRSLRSEDTAVYYCARDSGYDFEDWFDPWGQGTLVTVSS

Anti-LAG3 antibody 5C8:  Light chain variable region:  SEQ ID NO:9
QSVLTQPPSASGTPGQRVTISCSGSSSNIGSNTVNWYQQLPGTAPKLLIYSNNQRPSGVPDRFS
GSKSGNTASLTVSGLQAEDEADYYCAAWDDSLSGVVFGGGTQLTVL

Anti-LAG3 antibody 8D9:  Heavy chain variable region:  SEQ ID NO:10
QVQLVQSGAEVRKPGSSVKVSCKASGGTFSNYAFSWVRQAPGLGLEWLGAIIPEFDTANYAQKF
KDRVTITADDSTTTVYMELSSLRSEDTAVYYCASGMWDYYGSGSSIDYWGQGTLVTVSS

Anti-LAG3 antibody 8D9:  Light chain variable region:  SEQ ID NO:11
QSVLTQPPSASGTPGQRVTISCSGSNSDIGRNPVNWYHQFPGTAPKLLIFSNSHRPSGVPDRFS
GSKSGTSASLAIGGLQSDDEADYYCAAWSDSLNGYVFGTGTKLTVL

FIG. 2

ENGINEERED ANTIBODIES THAT BIND LAG3

CROSS-REFERENCE TO RELATED APPLICATIONS

This application is a national phase entry pursuant to 35 U.S.C. (371 of International Application No. PCT/US2021/025423, filed Apr. 1, 2021, which claims the benefit of priority of U.S. Provisional Patent Application No. 63/004,798, filed Apr. 3, 2020, each of which are incorporated by reference herein in their entireties for all purposes.

Throughout this application various publications, patents, and/or patent applications are referenced. The disclosures of the publications, patents and/or patent applications are hereby incorporated by reference in their entireties into this application in order to more fully describe the state of the art to which this disclosure pertains. To the extent any material incorporated by reference conflicts with the express content of this application, the express content controls.

SEQUENCE LISTING

The instant application contains a Sequence Listing which has been submitted electronically in ASCII format and is hereby incorporated by reference in its entirety. Said ASCII copy, created on Jan. 14, 2021, is named 2021-01-14_01223-0075-00PCT_Seq_List_ST25.txt and is 23,793 bytes in size.

TECHNICAL FIELD

The present disclosure provides fully human anti-LAG3 IgG class antibodies engineered to have amino acid sequence in their heavy chain variable region and/or light chain variable region to improve antigen binding, cell binding, T cell activation and cytokine release capabilities.

INTRODUCTION AND SUMMARY

Lymphocyte Activation Gene-3, or LAG3 (also known as CD223), is a member of the immunoglobulin supergene family and is structurally and genetically related to CD4. LAG3 is not expressed on resting peripheral blood lymphocytes but is expressed on activated T cells and NK cells. LAG3 is a membrane protein encoded by a gene located on the distal part of the short arm of chromosome 12, near the CD4 gene, suggesting that the LAG3 gene may have evolved through gene duplication (Triebel et al. (1990) *J. Exp. Med.* 171:1393-1405).

Similar to CD4, LAG3 has been demonstrated to interact with MHC Class II molecules but, unlike CD4, LAG3 does not interact with the human immunodeficiency virus gp120 protein (Baixeras et al. (1992) *J. Exp. Med.* 176:327-337). Studies using a soluble LAG3 immunoglobulin fusion protein (sLAG3Ig) demonstrated direct and specific binding of LAG3 to MHC class II on the cell surface (Huard et al. (1996) *Eur. J Immunol.* 26:1180-1186).

In in vitro studies of antigen-specific T cell responses, the addition of anti-LAG3 antibodies led to increased T cell proliferation, higher expression of activation antigens such as CD25, and higher concentrations of cytokines such as interferon-gamma and interleukin-4, supporting a role for the LAG3/MHC class II interaction in down-regulating antigen-dependent stimulation of CD4$^+$ T lymphocytes (Huard et al. (1994) *Eur. J Immunol.* 24:3216-3221). The intra-cytoplasmic region of LAG3 has been demonstrated to interact with a protein termed LAP, which is thought to be a signal transduction molecule involved in the downregulation of the CD3/TCR activation pathway (Iouzalen et al. (2001) *Eur. J. Immunol.* 31:2885-2891). Furthermore, CD4$^+$ CD25$^+$ regulatory T cells (T$_{reg}$) have been shown to express LAG3 upon activation and antibodies to LAG3 inhibit suppression by induced T$_{reg}$ cells, both in vitro and in vivo, suggesting that LAG3 contributes to the suppressor activity of T$_{reg}$ cells (Huang, C. et al. (2004) *Immunity* 21:503-513). Still further, LAG3 has been shown to negatively regulate T cell homeostasis by regulatory T cells in both T cell-dependent and independent mechanisms (Workman and Vignali (2005) *J. Immunol.* 174:688-695).

In certain circumstances, LAG3 also has been shown to have immunostimulatory effects. For example, LAG3 transfected tumor cells transplanted into syngeneic mice showed growth reduction or complete regression as compared to untransfected tumor cells, suggesting that LAG3 expression on the tumor cells stimulated an anti-tumor response by triggering antigen LAG3 presenting cells via MHC class II molecules (Prigent et al. (1999) *Eur. J. Immunol.* 29:3867-3876). Additionally, soluble LAG3 Ig fusion protein has been shown to stimulate both humoral and cellular immune responses when administered to mice together with an antigen, indicating that soluble LAG3Ig can function as a vaccine adjuvant (El Mir and Triebel (2000) *J. Immunol.* 164:5583-5589). Furthermore, soluble human LAG3Ig has been shown to amplify in vitro generation of type I tumor-specific immunity (Casati et al. (2006) *Cancer Res.* 66:4450-4460). The functional activity of LAG3 is reviewed further in Triebel (2003) *Trends Immunol.* 24:619-622. In view of the above, additional agents for modulating the activity of LAG3 are of interest.

There remains a need in the art for effective treatments based on LAG3, particularly anti-LAG3 antibodies. The present disclosure provides antibodies engineered to exhibit higher affinity binding to their target antigen and improved cell killing capabilities compared to the parent antibody. The disclosure includes the following embodiments. Embodiment 1 is a fully human anti-LAG3 antibody, comprising a heavy chain variable region having at least 95% sequence identity to the amino acid sequence of SEQ ID NO:4, 6, 8 or 10; and comprising a light chain variable region having at least 95% sequence identity to the amino acid sequence of SEQ ID NO:5, 7, 9 or 11.

Embodiment 2 is a LAG3-binding protein comprising a heavy chain variable region and a light chain variable region, wherein the heavy chain variable region comprises the CDR1, CDR2, and CDR3 sequences present in SEQ ID NO:4, 6, 8 or 10; and the light chain variable region comprises the CDR1, CDR2, and CDR3 sequences present in SEQ ID NO:5, 7, 9 or 11.

Embodiment 3 is the LAG3-binding protein of embodiment 2, wherein the heavy chain variable region comprises the CDR1, CDR2, and CDR3 sequences present in SEQ ID NO:4 and the light chain variable region comprises the CDR1, CDR2, and CDR3 sequences present in SEQ ID NO:5; or the heavy chain variable region comprises the CDR1, CDR2, and CDR3 sequences present in SEQ ID NO:6 and the light chain variable region comprises the CDR1, CDR2, and CDR3 sequences present in SEQ ID NO:7; or the heavy chain variable region comprises the CDR1, CDR2, and CDR3 sequences present in SEQ ID NO:8 and the light chain variable region comprises the CDR1, CDR2, and CDR3 sequences present in SEQ ID NO:9; or the heavy chain variable region comprises the CDR1, CDR2, and CDR3 sequences present in SEQ ID NO:10 and the light chain variable region comprises the CDR1, CDR2, and CDR3 sequences present in SEQ ID NO: 11.

Embodiment 4 is the LAG3-binding protein of embodiment 2 or 3, which is an antibody or antibody fragment.

Embodiment 5 is the fully human anti-LAG3 antibody of embodiment 1 or the LAG3-binding protein of any one of embodiments 2-4, wherein the heavy chain variable region sequence and the light chain variable region sequence comprise SEQ ID NOS:4 and 5 (called 1C5-3A6 herein), SEQ ID NOS:6 and 7 (called 2D12-2E3-N102D herein), SEQ ID NOS:8 and 9 (called 5C8 herein), or SEQ ID NOS:10 and 11 (called 8D9 herein).

Embodiment 6 is a Fab fully human anti-LAG3 antibody, comprising a variable domain region from a heavy chain and a variable domain region from a light chain, wherein the variable domain region from the heavy chain comprises a sequence having at least 95% sequence identity to the amino acid sequence of SEQ ID NO:4, 6, 8 or 10, and wherein the variable domain region from the light chain comprises a sequence having at least 95% sequence identity to the amino acid sequence of SEQ ID NO:5, 7, 9 or 11.

Embodiment 7 is the Fab fully human anti-LAG3 antibody of embodiment 6, wherein the variable domain region from the heavy chain and the variable domain region from the light chain comprise SEQ ID NOS:4 and 5 (called 1C5-3A6 herein), SEQ ID NOS:6 and 7 (called 2D12-2E3-N102D herein), SEQ ID NOS:8 and 9 (called 5C8 herein), or SEQ ID NOS:10 and 11 (called 8D9 herein).

Embodiment 8 is a single chain human anti-LAG3 antibody, comprising a variable domain region from a heavy chain and a variable domain region from a light chain, wherein the variable domain region from the heavy chain comprises a sequence having at least 95% sequence identity to the amino acid sequence of SEQ ID NO:4, 6, 8 or 10, and wherein the variable domain region from the light chain comprises a sequence having at least 95% sequence identity to the amino acid sequence of SEQ ID NO:5, 7, 9 or 11.

Embodiment 9 is the LAG3-binding protein of any one of embodiments 2-5 or the single chain human anti-LAG3 antibody of embodiment 8, wherein the variable domain region from a heavy chain and the variable domain region from a light chain are joined together with a peptide linker.

Embodiment 10 is the single chain human anti-LAG3 antibody of embodiment 8, wherein the variable domain region from the heavy chain and the variable domain region from the light chain comprise SEQ ID NOS:4 and 5 (called 1C5-3A6 herein), SEQ ID NOS:6 and 7 (called 2D12-2E3-N102D herein), SEQ ID NOS:8 and 9 (called 5C8 herein), or SEQ ID NOS:10 and 11 (called 8D9 herein).

Embodiment 11 is the LAG3-binding protein or fully human anti-LAG3 antibody of any one of the preceding embodiments, wherein the antibody binds human LAG3 with a $K_D$ of $10^{-8}$ M or less.

Embodiment 12 is the LAG3-binding protein or fully human anti-LAG3 antibody of any one of embodiments 1-7, wherein the antibody binds cynomolgus LAG3 with a $K_D$ of $10^{-6}$ M or less.

Embodiment 13 is the LAG3-binding protein or fully human anti-LAG3 antibody of any one of the preceding embodiments, comprising an IgG4 class antibody.

Embodiment 14 is a pharmaceutical composition, comprising a pharmaceutically-acceptable excipient and the LAG3-binding protein or fully human anti-LAG3 antibody of any one of the preceding embodiments.

Embodiment 15 is a kit comprising the LAG3-binding protein, Fab fully human anti-LAG3 antibody, single chain human anti-LAG3 antibody, or fully human anti-LAG3 antibody of any one of embodiments 1-13.

Embodiment 16 is a nucleic acid that encodes the heavy chain variable region of the LAG3-binding protein or fully human anti-LAG3 antibody of any one of embodiments 1-13.

Embodiment 17 is a nucleic acid that encodes the light chain variable region of the LAG3-binding protein or fully human anti-LAG3 antibody of any one of embodiments 1-13.

Embodiment 18 is a nucleic acid that encodes (a)(i) the heavy chain variable region of the fully human anti-LAG3 antibody of any one of embodiments 1-13, and (ii) the light chain variable region of the fully human anti-LAG3 antibody of any of embodiments 1-13; or (b) the LAG3-binding protein of any one of embodiments 2-5, 9, or 11-13.

Embodiment 19 is a vector comprising the nucleic acid of embodiment 16.

Embodiment 20 is a vector comprising the nucleic acid of embodiment 17.

Embodiment 21 is a vector comprising the nucleic acid of embodiment 18.

Embodiment 22 is a host cell harboring the vector of embodiment 19.

Embodiment 23 is the host cell of embodiment 22, wherein the vector comprises an expression vector, and wherein the host cell expresses the heavy chain variable region.

Embodiment 24 is a host cell harboring the vector of embodiment 20.

Embodiment 25 is the host cell of embodiment 24, wherein the vector comprises an expression vector, and wherein the host cell expresses the light chain variable region.

Embodiment 26 is a host cell harboring a first vector comprising the vector of embodiment 19 and a second vector comprising the vector of embodiment 20.

Embodiment 27 is the host cell of embodiment 26, wherein the first vector comprises a first expression vector, wherein the second vector comprises a second expression vector, and wherein the host cell expresses the heavy and the light chain variable regions.

Embodiment 28 is a host cell harboring the vector of embodiment 21.

Embodiment 29 is the host cell of embodiment 28, wherein the vector comprises an expression vector, and wherein the host cell expresses the heavy and the light chain variable regions.

Embodiment 30 is a method for preparing a LAG3-binding protein, or a heavy chain variable region of a fully human anti-LAG3 antibody, or a Fab fully human anti-LAG3 antibody, or a single chain human anti-LAG3 antibody, the method comprising: culturing a population of the host cell of embodiment 23 under conditions suitable for expressing the heavy chain variable region of the fully human anti-LAG3 antibody, or the Fab fully human anti-LAG3 antibody, or the single chain human anti-LAG3 antibody.

Embodiment 31 is the method of embodiment 30, further comprising: recovering from the host cells the expressed LAG3-binding protein, or the heavy chain variable region of the fully human anti-LAG3 antibody, or the Fab fully human anti-LAG3 antibody, or the single chain human anti-LAG3 antibody.

Embodiment 32 is a method for preparing a light chain variable region of a fully human anti-LAG3 antibody, or a Fab fully human anti-LAG3 antibody, or a single chain human anti-LAG3 antibody, the method comprising: culturing a population of the host cell of embodiment 25 under conditions suitable for expressing the light chain variable region of the fully human anti-LAG3 antibody, or the Fab fully human anti-LAG3 antibody, or the single chain human anti-LAG3 antibody.

Embodiment 33 is the method of embodiment 32, further comprising: recovering from the host cells the expressed light chain variable region of the fully human anti-LAG3 antibody, or the Fab fully human anti-LAG3 antibody, or the single chain human anti-LAG3 antibody.

Embodiment 34 is a method for preparing (i) a heavy chain variable region of a fully human anti-LAG3 antibody, or a Fab fully human anti-LAG3 antibody, or a single chain human anti-LAG3 antibody, and (ii) a light chain variable region of a fully human anti-LAG3 antibody, or a Fab fully human anti-LAG3 antibody, or a single chain human anti-LAG3 antibody, the method comprising: culturing a population of the host cell of embodiment 27 under conditions suitable for expressing (i) the heavy chain variable region of the fully human anti-LAG3 antibody, or the Fab fully human anti-LAG3 antibody, or the single chain human anti-LAG3 antibody, and (ii) the light chain variable region of the fully human anti-LAG3 antibody, or the Fab fully human anti-LAG3 antibody, or the single chain human anti-LAG3 antibody.

Embodiment 35 is the method of embodiment 34, further comprising: recovering from the host cells (i) the expressed heavy chain variable region of the fully human anti-LAG3 antibody, or the Fab fully human anti-LAG3 antibody, or the single chain human anti-LAG3 antibody, and (ii) the expressed light chain variable region of the fully human anti-LAG3 antibody, or the Fab fully human anti-LAG3 antibody, or the single chain human anti-LAG3 antibody.

Embodiment 36 is a method for preparing (i) a heavy chain variable region of a fully human anti-LAG3 antibody, or a Fab fully human anti-LAG3 antibody, or a single chain human anti-LAG3 antibody, and (ii) a light chain variable region of a fully human anti-LAG3 antibody, or a Fab fully human anti-LAG3 antibody, or a single chain human anti-LAG3 antibody, the method comprising: culturing a population of the host cell of embodiment 29 under conditions suitable for expressing (i) the heavy chain variable region of the fully human anti-LAG3 antibody, or the Fab fully human anti-LAG3 antibody, or the single chain human anti-LAG3 antibody, and (ii) the light chain variable region of the fully human anti-LAG3 antibody, or the Fab fully human anti-LAG3 antibody, or the single chain human anti-LAG3 antibody.

Embodiment 37 is the method of embodiment 36, further comprising: recovering from the host cells (i) the expressed heavy chain variable region of the fully human anti-LAG3 antibody, or the Fab fully human anti-LAG3 antibody, or the single chain human anti-LAG3 antibody, and (ii) the expressed light chain variable region of the fully human anti-LAG3 antibody, or the Fab fully human anti-LAG3 antibody, or the single chain human anti-LAG3 antibody.

Embodiment 38 is a method for treating a subject having a disease associated with LAG3 over-expression, the method comprising: administering to the subject an effective amount of a therapeutic composition comprising the LAG3-binding protein or human anti-LAG3 antibody of any one of embodiments 1-13.

Embodiment 39 is the LAG3-binding protein or human anti-LAG3 antibody of any one of embodiments 1-13, for use in treating a disease associated with LAG3 over-expression.

Embodiment 40 is the method of embodiment 38, or the LAG3-binding protein or human anti-LAG3 antibody for use of embodiment 39, wherein the disease is bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancer, or a cancer induced by asbestos.

Embodiment 41 is the LAG3-binding protein or human anti-LAG3 antibody of any one of embodiments 1-13, for use in the method of any one of embodiments 38.

DESCRIPTION OF THE DRAWINGS

FIG. 1 shows the amino acid sequences of LAG3 target antigen from human (SEQ ID NO:1), cynomolgus monkey (SEQ ID NO:2), and mouse (SEQ ID NO:3).

FIG. 2 shows the amino acid sequences of heavy chain variable regions and light chain variable regions of fully human anti-LAG3 antibodies 1C5-3A6 (SEQ ID NOS:4 and 5), 2D12-2E3-N102D (SEQ ID NOS:6 and 7), 5C8 (SEQ ID NOS:8 and 9), and 8D9 (SEQ ID NOS:10 and 11).

7 cell activated with Staphylococcal Enterotoxin (SEB). Experiment #1 is described in Example 6.

Figure 8A:
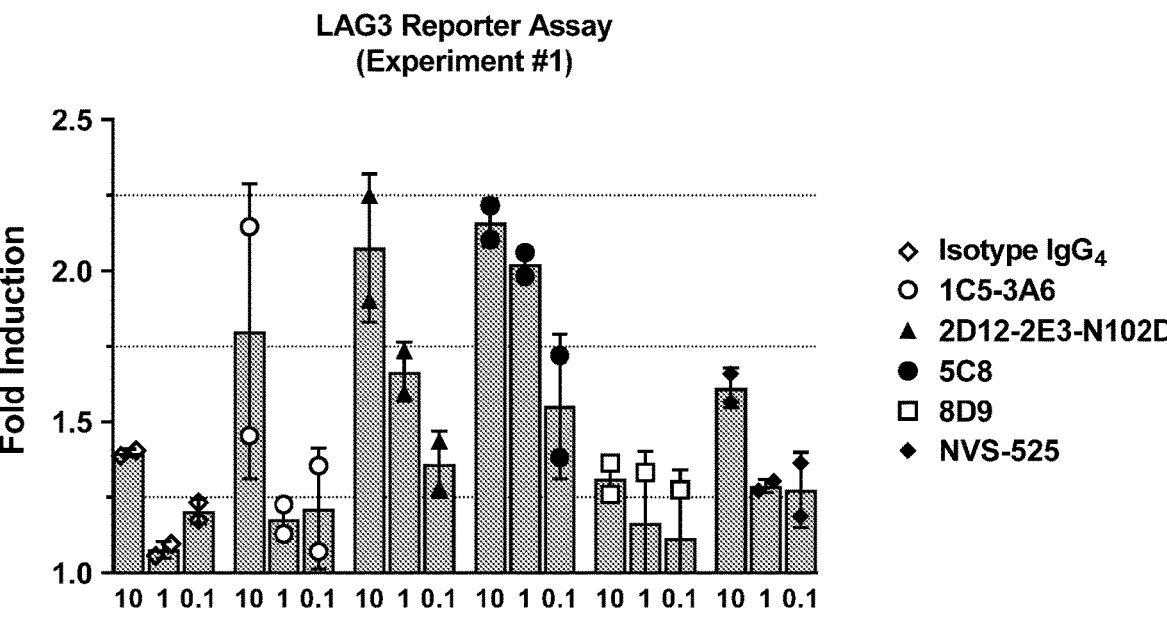
FIG. 8A is a bar graph comparing functional activity of various anti-LAG3 antibodies in presence of a reporter Jurkat cell line expressing human LAG3/NFAT-Luc and Raji
Figure 8B:
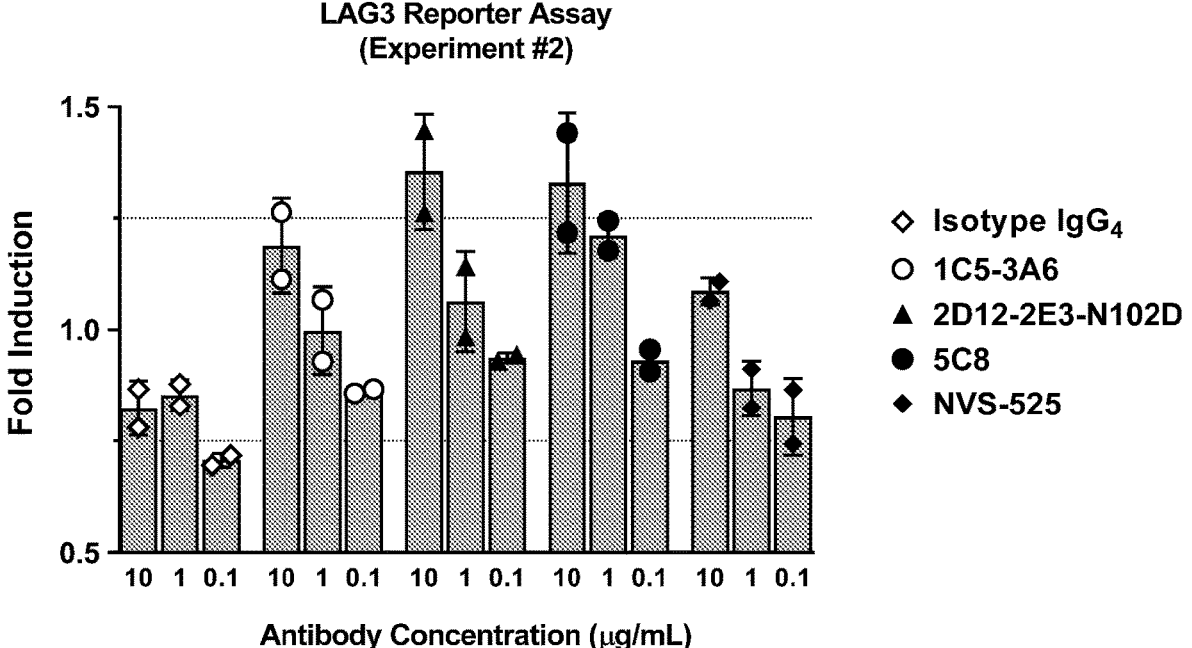

FIG. 8B is a bar graph comparing functional activity of various anti-LAG3 antibodies in presence of a reporter Jurkat cell line expressing human LAG3/NFAT-Luc and Raji cell activated with Staphylococcal Enterotoxin (SEB). Experiment #2 is described in Example 6.

Figure 9:
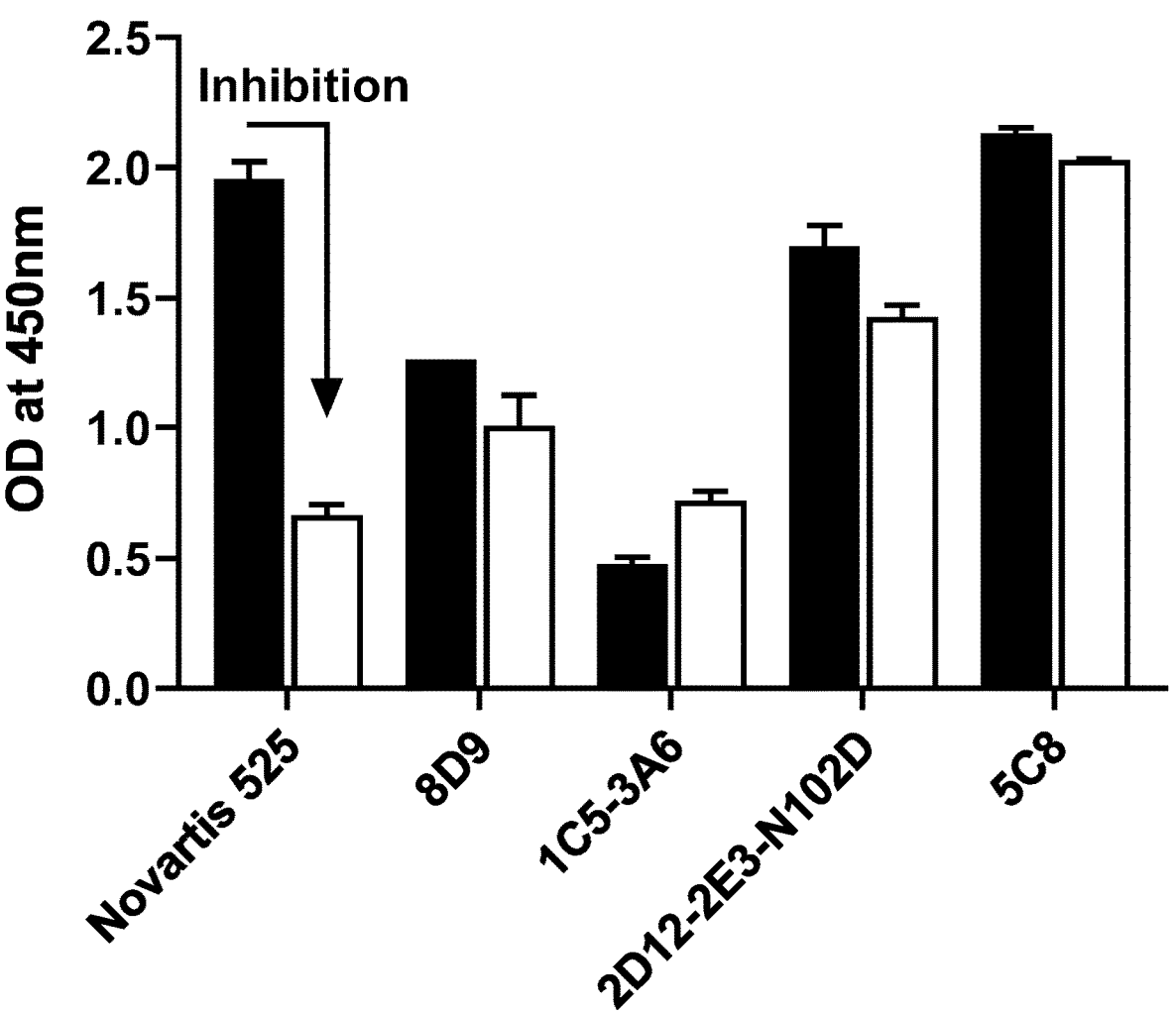

FIG. 9 is a bar graph showing the results of an epitope mapping assay, comparing binding of anti-LAG3 antibodies described herein and a competitor's anti-LAG3 antibody. The experiment is described in Example 7.

Figure 10A:
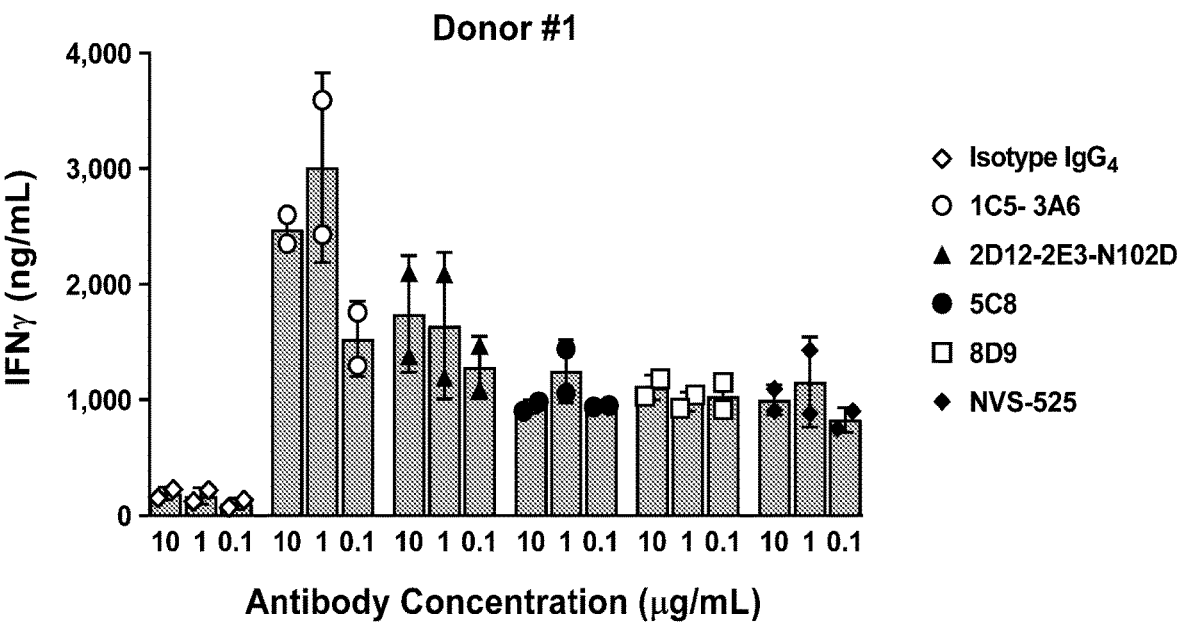

FIG. 10A is a bar graph comparing interferon-gamma release induced by various anti-LAG3 antibodies using PBMCs from donor #1. The experiment is described in Example 8.

Figure 10B:
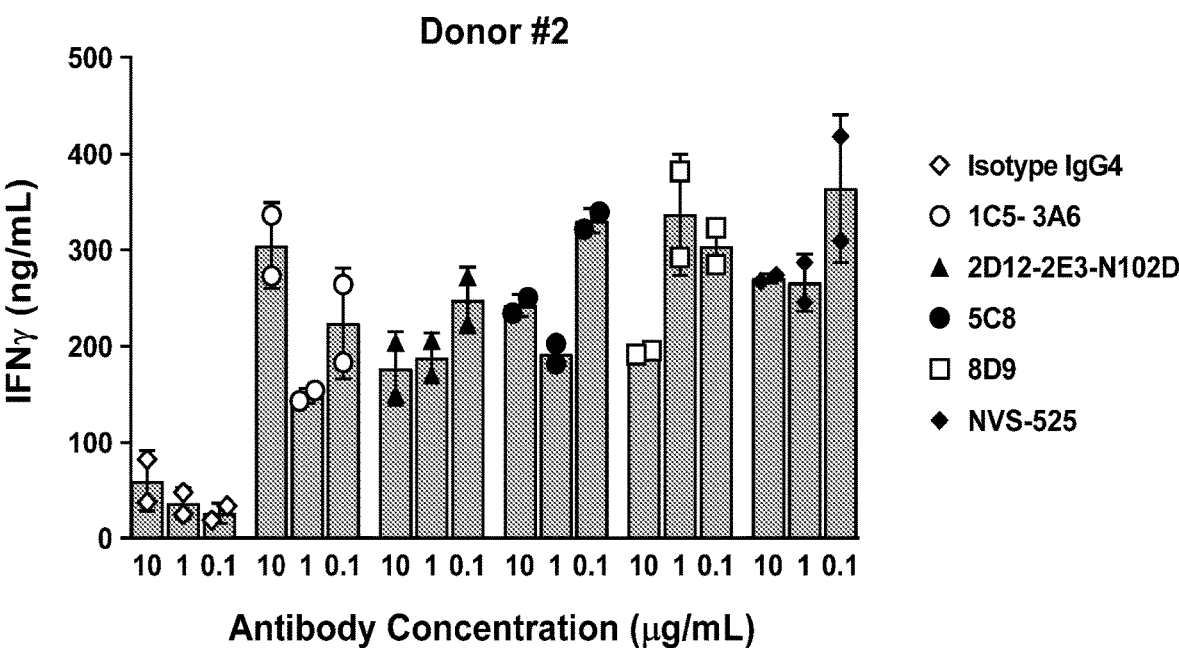

FIG. 10B is a bar graph comparing interferon-gamma release induced by various anti-LAG3 antibodies using PBMCs from donor #2. The experiment is described in Example 8.

DEFINITIONS

Unless defined otherwise, technical and scientific terms used herein have meanings that are commonly understood by those of ordinary skill in the art unless defined otherwise. Generally, terminologies pertaining to techniques of cell and tissue culture, molecular biology, immunology, microbiology, genetics, transgenic cell production, protein chemistry and nucleic acid chemistry and hybridization described herein are well known and commonly used in the art. The methods and techniques provided herein are generally performed according to conventional procedures well known in the art and as described in various general and more specific references that are cited and discussed herein unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992). A number of basic texts describe standard antibody production processes, including, Borrebaeck (ed) *Antibody Engineering, 2nd Edition* Freeman and Company, NY, 1995; McCafferty et al. *Antibody Engineering, A Practical Approach* IRL at Oxford Press, Oxford, England, 1996; and Paul (1995) *Antibody Engineering Protocols* Humana Press, Towata, N.J., 1995; Paul (ed.), *Fundamental Immunology*, Raven Press, N.Y, 1993; Coligan (1991) *Current Protocols in Immunology* Wiley/Greene, NY; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; *Coding Monoclonal Antibodies: Principles and Practice* (2nd ed.) Academic Press, New York, N.Y., 1986, and Kohler and Milstein *Nature* 256: 495-497, 1975. All of the references cited herein are incorporated herein by reference in their entireties. Enzymatic reactions and enrichment/purification techniques are also well known and are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are well known and commonly used in the art. Standard techniques can be used for chemical syntheses, chemical analyses, pharmaceutical preparation, formulation, and delivery, and treatment of patients.

The headings provided herein are not limitations of the various aspects of the disclosure, which aspects can be understood by reference to the specification as a whole.

Unless otherwise required by context herein, singular terms shall include pluralities and plural terms shall include the singular. Singular forms "a", "an" and "the", and singular use of any word, include plural referents unless expressly and unequivocally limited on one referent.

It is understood the use of the alternative (e.g., "or") herein is taken to mean either one or both or any combination thereof of the alternatives.

The term "and/or" used herein is to be taken mean specific disclosure of each of the specified features or components with or without the other. For example, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, terms "comprising", "including", "having" and "containing", and their grammatical variants, as used herein are intended to be non-limiting so that one item or multiple items in a list do not exclude other items that can be substituted or added to the listed items. It is understood that wherever aspects are described herein with the language "comprising," otherwise analogous aspects described in terms of "consisting of" and/or "consisting essentially of" are also provided.

As used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "approximately" can mean within one or more than one standard deviation per the practice in the art. Alternatively, "about" or "approximately" can mean a range of up to 10% (i.e., ±10%) or more depending on the limitations of the measurement system. For example, about 5 mg can include any number between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "approximately" should be assumed to be within an acceptable error range for that particular value or composition.

The terms "peptide", "polypeptide" and "protein" and other related terms used herein are used interchangeably and refer to a polymer of amino acids and are not limited to any particular length. Polypeptides may comprise natural and non-natural amino acids. Polypeptides include recombinant or chemically-synthesized forms. Polypeptides also include precursor molecules that have not yet been subjected to cleavage, for example cleavage by a secretory signal peptide or by non-enzymatic cleavage at certain amino acid residues. Polypeptides include mature molecules that have undergone cleavage. These terms encompass native and artificial proteins, protein fragments and polypeptide analogs (such as muteins, variants, chimeric proteins and fusion proteins) of a protein sequence as well as post-translationally, or otherwise covalently or non-covalently, modified proteins. Polypeptides comprising amino acid sequences of binding proteins that bind LAG3 (e.g., anti-LAG3 antibodies or antigen-binding portions thereof) prepared using recombinant procedures are described herein.

The terms "nucleic acid", "polynucleotide" and "oligo-nucleotide" and other related terms used herein are used interchangeably and refer to polymers of nucleotides and are not limited to any particular length. Nucleic acids include recombinant and chemically-synthesized forms. Nucleic acids include DNA molecules (cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. Nucleic acid molecule can be single-stranded or double-stranded. In one embodiment, the nucleic acid molecules of the disclosure comprise a contiguous open reading frame encoding an antibody, or a fragment or scFv, derivative, mutein, or variant thereof. In one embodiment, nucleic acids comprise a one type of polynucleotides or a mixture of two or more different types of polynucleotides. Nucleic acids encoding the antibody light chains, antibody heavy chains, anti-LAG3 antibodies or antigen-binding portions thereof, are described herein. In one embodiment, nucleic acids encode a heavy chain variable region comprising at least 95% sequence identity to the amino acid sequence of SEQ ID NO:4, 6, 8 or 10. In one embodiment, nucleic acids encode a light chain variable region comprising at least 95% sequence identity to the amino acid sequence of SEQ ID NO:5, 7, 9 or 11.

The term "recover" or "recovery" or "recovering", and other related terms, refers to obtaining a protein (e.g., an antibody or an antigen binding portion thereof), from host cell culture medium or from host cell lysate or from the host cell membrane. In one embodiment, the protein is expressed by the host cell as a recombinant protein fused to a secretion signal peptide sequence which mediates secretion of the expressed protein. The secreted protein can be recovered from the host cell medium. In one embodiment, the protein is expressed by the host cell as a recombinant protein that lacks a secretion signal peptide sequence which can be recovered from the host cell lysate. In one embodiment, the protein is expressed by the host cell as a membrane-bound protein which can be recovered using a detergent to release the expressed protein from the host cell membrane. In one embodiment, irrespective of the method used to recover the protein, the protein can be subjected to procedures that remove cellular debris from the recovered protein. For example, the recovered protein can be subjected to chromatography, gel electrophoresis and/or dialysis. In one embodiment, the chromatography comprises any one or any combination or two or more procedures including affinity chromatography, hydroxyapatite chromatography, ion-exchange chromatography, reverse phase chromatography and/or chromatography on silica. In one embodiment, affinity chromatography comprises protein A or G (cell wall components from *Staphylococcus aureus*).

The term "isolated" refers to a protein (e.g., an antibody or an antigen binding portion thereof) or polynucleotide that is substantially free of other cellular material. A protein may be rendered substantially free of naturally associated components (or components associated with a cellular expression system or chemical synthesis methods used to produce the antibody) by isolation, using protein purification techniques well known in the art. The term isolated also refers in some embodiments to protein or polynucleotides that are substantially free of other molecules of the same species, for example other protein or polynucleotides having different amino acid or nucleotide sequences, respectively. The purity of homogeneity of the desired molecule can be assayed using techniques well known in the art, including low resolution methods such as gel electrophoresis and high resolution methods such as HPLC or mass spectrophotometry. In one embodiment, any of the antibody light chains, antibody heavy chains, anti-LAG3 antibodies or antigen binding protein described herein can be isolated.

An "antigen binding protein" and related terms used herein (e.g., LAG3-binding protein) refers to a protein comprising a portion that binds to an antigen (e.g., LAG3) and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a bio-compatible polymer. See, for example, Korndorfer et al., 2003, Proteins: Structure, Function, and Bioinformatics, Volume 53, Issue 1:121-129; Roque et al., 2004, Biotechnol. Prog. 20:639-654. In addition, peptide antibody mimetics ("PAMs") can be used, as well as scaffolds based on antibody mimetics utilizing fibronection components as a scaffold. Antigen binding proteins that bind LAG3 are described herein.

An antigen binding protein can have, for example, the structure of an immunoglobulin. In one embodiment, an "immunoglobulin" refers to a tetrameric molecule composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two antigen binding sites. In one embodiment, an antigen binding protein can be a synthetic molecule having a structure that differs from a tetrameric immunoglobulin molecule but still binds a target antigen or binds two or more target antigens. For example, a synthetic antigen binding protein can comprise antibody fragments, 1-6 or more polypeptide chains, asymmetrical assemblies of polypeptides, or other synthetic molecules. Antigen binding proteins having immunoglobulin-like properties that bind specifically to LAG3 are described herein.

The variable regions of immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4.

One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

The assignment of amino acids to each domain is in accordance with the definitions of Kabat et al. in Sequences of Proteins of Immunological Interest, $5^{th}$ Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, *Dev. Comp. Immunol.* 29:185-203; 2005) and AHo (Honegger and Pluckthun, *J. Mol. Biol.* 309(3):657-670; 2001); Chothia (Al-Lazikani et al., 1997 Journal of Molecular Biology 273:927-948; Contact (Maccallum et al., 1996 Journal of Molecular Biology 262:732-745, and Aho (Honegger and Pluckthun 2001 Journal of Molecular Biology 309:657-670.

An "antibody" and "antibodies" and related terms used herein refers to an intact immunoglobulin or to an antigen binding portion thereof that binds specifically to an antigen. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

Antibodies include recombinantly produced antibodies and antigen binding portions. Antibodies include non-human, chimeric, humanized and fully human antibodies. Antibodies include monospecific, multispecific (e.g., bispecific, trispecific and higher order specificities). Antibodies include tetrameric antibodies, light chain monomers, heavy chain monomers, light chain dimers, heavy chain dimers. Antibodies include F(ab')$_2$ fragments, Fab' fragments and Fab fragments. Antibodies include single domain antibodies, monovalent antibodies, single chain antibodies, single chain variable fragment (scFv), camelized antibodies, affibodies, disulfide-linked Fvs (sdFv), anti-idiotypic antibodies (anti-Id), minibodies. Antibodies include monoclonal and polyclonal populations. Anti-LAG3 antibodies, comprising light and/or heavy chains are described herein.

An "antigen binding domain," "antigen binding region," or "antigen binding site" and other related terms used herein refer to a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains. Antigen binding domains from anti-LAG3 antibodies are described herein.

The terms "specific binding", "specifically binds" or "specifically binding" and other related terms, as used herein in the context of an antibody or antigen binding protein or antibody fragment, refer to non-covalent or covalent preferential binding to an antigen relative to other molecules or moieties (e.g., an antibody specifically binds to a particular antigen relative to other available antigens). In one embodiment, an antibody specifically binds to a target antigen if it binds to the antigen with a dissociation constant $K_D$ of $10^{-5}$ M or less, or $10^{-6}$ M or less, or $10^{-7}$ M or less, or $10^{-8}$ M or less, or $10^{-9}$ M or less, or $10^{-10}$ M or less. Anti-LAG3 antibodies that specifically bind LAG3 are described herein.

In one embodiment, a dissociation constant ($K_D$) can be measured using a BIACORE surface plasmon resonance (SPR) assay. Surface plasmon resonance refers to an optical phenomenon that allows for the analysis of real-time interactions by detection of alterations in protein concentrations within a biosensor matrix, for example using the BIACORE system (Biacore Life Sciences division of GE Healthcare, Piscataway, N.J.).

An "epitope" and related terms as used herein refers to a portion of an antigen that is bound by an antigen binding protein (e.g., by an antibody or an antigen binding portion thereof). An epitope can comprise portions of two or more antigens that are bound by an antigen binding protein. An epitope can comprise non-contiguous portions of an antigen or of two or more antigens (e.g., amino acid residues that are not contiguous in an antigen's primary sequence but that, in the context of the antigen's tertiary and quaternary structure, are near enough to each other to be bound by an antigen binding protein). Generally, the variable regions, particularly the CDRs, of an antibody interact with the epitope. Anti-LAG3 antibodies, and antigen binding proteins thereof, that bind an epitope of a LAG3 polypeptide (antigen) are described herein.

An "antibody fragment", "antibody portion", "antigen-binding fragment of an antibody", or "antigen-binding portion of an antibody" and other related terms used herein refer to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; Fd; and Fv fragments, as well as dAb; diabodies; linear antibodies; single-chain antibody molecules (e.g. scFv); polypeptides that contain at least a portion of an antibody that is sufficient to confer specific antigen binding to the polypeptide. Antigen binding portions of an antibody may be produced by recombinant DNA techniques or by enzymatic or chemical cleavage of intact antibodies. Antigen binding portions include, inter alia, Fab, Fab', F(ab')2, Fv, domain antibodies (dAbs), and complementarity determining region (CDR) fragments, chimeric antibodies, diabodies, triabodies, tetrabodies, and polypeptides that contain at least a portion of an immunoglobulin that is sufficient to confer antigen binding properties to the antibody fragment. Antigen-binding fragments of anti-LAG3 antibodies are described herein.

The terms "Fab", "Fab fragment" and other related terms refers to a monovalent fragment comprising a variable light chain region ($V_L$), constant light chain region (CL), variable heavy chain region ($V_H$), and first constant region ($C_{H1}$). A Fab is capable of binding an antigen. An F(ab')$_2$ fragment is a bivalent fragment comprising two Fab fragments linked by a disulfide bridge at the hinge region. A F(Ab')$_2$ has antigen binding capability. An Fd fragment comprises $V_H$ and $C_{H1}$ regions. An Fv fragment comprises $V_L$ and $V_H$ regions. An Fv can bind an antigen. A dAb fragment has a $V_H$ domain, a $V_L$ domain, or an antigen-binding fragment of a $V_H$ or $V_L$ domain (U.S. Pat. Nos. 6,846,634 and 6,696,245; U.S. published Application Nos. 2002/02512, 2004/0202995, 2004/0038291, 2004/0009507, 2003/0039958; and Ward et al., Nature 341:544-546, 1989). Fab fragments comprising antigen binding portions from anti-LAG3 antibodies are described herein.

A single-chain antibody (scFv) is an antibody in which a $V_L$ and a $V_H$ region are joined via a linker (e.g., a synthetic sequence of amino acid residues) to form a continuous protein chain. Preferably the linker is long enough to allow the protein chain to fold back on itself and form a monovalent antigen binding site (see, e.g., Bird et al., 1988, Science 242:423-26 and Huston et al., 1988, Proc. Natl. Acad. Sci. USA 85:5879-83). Single chain antibodies comprising antigen binding portions from anti-LAG3 antibodies are described herein.

Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different. Diabody, tribody and tetrabody constructs can be prepared using antigen binding portions from any of the anti-LAG3 antibodies described herein.

The term "human antibody" refers to antibodies that have one or more variable and constant regions derived from human immunoglobulin sequences. In one embodiment, all of the variable and constant domains are derived from human immunoglobulin sequences (e.g., a fully human antibody). These antibodies may be prepared in a variety of ways, examples of which are described below, including through recombinant methodologies or through immunization with an antigen of interest of a mouse that is genetically modified to express antibodies derived from human heavy and/or light chain-encoding genes. Fully human anti-LAG3 antibodies and antigen binding proteins thereof are described herein.

A "humanized" antibody refers to an antibody having a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" and related terms used herein refers to an antibody that contains one or more regions from a first antibody and one or more regions from one or more other antibodies. In one embodiment, one or more of the CDRs are derived from a human antibody. In another embodiment, all of the CDRs are derived from a human antibody. In another embodiment, the CDRs from more than one human antibody are mixed and matched in a chimeric antibody. For instance, a chimeric antibody may comprise a CDR1 from the light chain of a first human antibody, a CDR2 and a CDR3 from the light chain of a second human antibody, and the CDRs from the heavy chain from a third antibody. In another example, the CDRs originate from different species such as human and mouse, or human and rabbit, or human and goat. One skilled in the art will appreciate that other combinations are possible.

Further, the framework regions may be derived from one of the same antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind a target antigen). Chimeric antibodies can be prepared from portions of any of the anti-LAG3 antibodies described herein.

As used herein, the term "variant" polypeptides and "variants" of polypeptides refers to a polypeptide comprising an amino acid sequence with one or more amino acid residues inserted into, deleted from and/or substituted into the amino acid sequence relative to a reference polypeptide sequence. Polypeptide variants include fusion proteins. In the same manner, a variant polynucleotide comprises a nucleotide sequence with one or more nucleotides inserted into, deleted from and/or substituted into the nucleotide sequence relative to another polynucleotide sequence. Polynucleotide variants include fusion polynucleotides.

As used herein, the term "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

The term "Fc" or "Fc region" as used herein refers to the portion of an antibody heavy chain constant region beginning in or after the hinge region and ending at the C-terminus of the heavy chain. The Fc region comprises at least a portion of the CH and CH3 regions and may, or may not, include a portion of the hinge region. Two polypeptide chains each carrying a half Fc region can dimerize to form a full Fc domain. An Fc domain can bind Fc cell surface receptors and some proteins of the immune complement system. An Fc domain exhibits effector function, including any one or any combination of two or more activities including complement-dependent cytotoxicity (CDC), antibody-dependent cell-mediated cytotoxicity (ADCC), antibody-dependent phagocytosis (ADP), opsonization and/or cell binding. An Fc domain can bind an Fc receptor, including FcγRI (e.g., CD64), FcγRII (e.g, CD32) and/or FcγRIII (e.g., CD16a).

The term "labeled antibody" or related terms as used herein refers to antibodies and their antigen binding portions thereof that are unlabeled or joined to a detectable label or moiety for detection, wherein the detectable label or moiety is radioactive, colorimetric, antigenic, enzymatic, a detectable bead (such as a magnetic or electrodense (e.g., gold) bead), biotin, streptavidin or protein A. A variety of labels can be employed, including, but not limited to, radionuclides, fluorescers, enzymes, enzyme substrates, enzyme cofactors, enzyme inhibitors and ligands (e.g., biotin, haptens). Any of the anti-LAG3 antibodies described herein can be unlabeled or can be joined to a detectable label or moiety.

The "percent identity" or "percent homology" and related terms used herein refers to a quantitative measurement of the similarity between two polypeptide or between two polynucleotide sequences. The percent identity between two polypeptide sequences is a function of the number of identical amino acids at aligned positions that are shared between the two polypeptide sequences, taking into account the number of gaps, and the length of each gap, which may need to be introduced to optimize alignment of the two polypeptide sequences. In a similar manner, the percent identity between two polynucleotide sequences is a function of the number of identical nucleotides at aligned positions that are shared between the two polynucleotide sequences, taking into account the number of gaps, and the length of each gap, which may need to be introduced to optimize alignment of the two polynucleotide sequences. A comparison of the sequences and determination of the percent identity between two polypeptide sequences, or between two polynucleotide sequences, may be accomplished using a mathematical algorithm. For example, the "percent identity" or "percent homology" of two polypeptide or two polynucleotide sequences may be determined by comparing the sequences using the GAP computer program (a part of the GCG Wisconsin Package, version 10.3 (Accelrys, San Diego, Calif.)) using its default parameters. Expressions such as "comprises a sequence with at least X % identity to Y" with respect to a test sequence mean that, when aligned to sequence Y as described above, the test sequence comprises residues identical to at least X % of the residues of Y.

In one embodiment, the amino acid sequence of a test antibody may be similar but not identical to any of the amino acid sequences of the light chain and/or heavy chain polypeptides that make up any of the anti-LAG3 antibodies, or antigen binding protein thereof, described herein. The similarities between the test antibody and the polypeptides can be at least 95%, or at or at least 96% identical, or at least 97% identical, or at least 98% identical, or at least 99% identical, to any of the light chain and/or heavy chain polypeptides that make up any of the anti-LAG3 antibodies, or antigen binding protein thereof, described herein. In one embodiment, similar polypeptides can contain amino acid substitutions within a heavy and/or light chain. In one embodiment, the amino acid substitutions comprise one or more conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. A skilled artisan can introduce up to 5% conservative and/or non-conservative amino acid substitutions in a heavy chain variable region and/or light chain variable region without negatively impacting the physical structure, binding capability or cell killing capability of an antibody. Well known methods for identifying and making conservative amino acid substitutions in a variable region that are designed to retain or improve antibody binding characteristics are described in: Brummel, et al., 1993 Biochemistry 32:1180-1187; Kobayashi et al., 1999 Protein Engineering 12(10):879-884; and Burks et al., 1997 Proc. Natl. Acad. Sci. USA 94:412-417). Methods for identifying and making non-conservative amino acid substitutions in a heavy chain and/or light chain variable region to retain or improve antigen binding are also known (Near et al., 1993 Molecular Immunology 30(4):369-377). Thus, a skilled artisan can predict and change up to 5% of the amino acids in a heavy chain variable region and/or light chain variable region without significantly diminishing antigen binding capability of an antibody. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference in its entirety. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen. Antibodies can be produced using recombinant nucleic acid technology as described below.

A "vector" and related terms used herein refers to a nucleic acid molecule (e.g., DNA or RNA) which can be operably linked to foreign genetic material (e.g., nucleic acid transgene). Vectors can be used as a vehicle to introduce foreign genetic material into a cell (e.g., host cell). Vectors can include at least one restriction endonuclease recognition sequence for insertion of the transgene into the vector. Vectors can include at least one gene sequence that confers antibiotic resistance or a selectable characteristic to aid in selection of host cells that harbor a vector-transgene construct. Vectors can be single-stranded or double-stranded nucleic acid molecules. Vectors can be linear or circular nucleic acid molecules. A donor nucleic acid used for gene editing methods employing zinc finger nuclease, TALEN or CRISPR/Cas can be a type of a vector. One type of vector is a "plasmid," which refers to a linear or circular double stranded extrachromosomal DNA molecule which can be linked to a transgene, and is capable of replicating in a host cell, and transcribing and/or translating the transgene. A viral vector typically contains viral RNA or DNA backbone sequences which can be linked to the transgene. The viral backbone sequences can be modified to disable infection but retain insertion of the viral backbone and the co-linked transgene into a host cell genome. Examples of viral vectors include retroviral, lentiviral, adenoviral, adeno-associated, baculoviral, papovaviral, vaccinia viral, herpes simplex viral and Epstein Barr viral vectors. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome.

An "expression vector" is a type of vector that can contain one or more regulatory sequences, such as inducible and/or constitutive promoters and enhancers. Expression vectors can include ribosomal binding sites and/or polyadenylation sites. Regulatory sequences direct transcription, or transcription and translation, of a transgene linked to the expression vector which is transduced into a host cell. The regulatory sequence(s) can control the level, timing and/or location of expression of the transgene. The regulatory sequence can, for example, exert its effects directly on the transgene, or through the action of one or more other molecules (e.g., polypeptides that bind to the regulatory sequence and/or the nucleic acid). Regulatory sequences can be part of a vector. Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-3606. An expression vector can comprise nucleic acids that encode at least a portion of any of the light chain, heavy chain or anti-LAG3 antibodies described herein.

Vectors (e.g., expression vectors) operably linked to a nucleic acid encoding the antibody light chains, antibody heavy chains, anti-LAG3 antibodies or antigen-binding portions thereof, are described herein. In one embodiment, a vector is operably linked a nucleic acid encoding a heavy chain variable region comprising at least 95% sequence identity to the amino acid sequence of SEQ ID NO:4, 6, 8 or 10. In one embodiment, nucleic acids encode a light chain variable region comprising at least 95% sequence identity to the amino acid sequence of SEQ ID NO:5, 7, 9 or 11.

A transgene is "operably linked" to a vector when there is linkage between the transgene and the vector to permit functioning or expression of the transgene sequences contained in the vector. In one embodiment, a transgene is "operably linked" to a regulatory sequence when the regulatory sequence affects the expression (e.g., the level, timing, or location of expression) of the transgene.

The terms "transfected" or "transformed" or "transduced" or other related terms used herein refer to a process by which exogenous nucleic acid (e.g., transgene) is transferred or introduced into a host cell. A "transfected" or "transformed" or "transduced" host cell is one which has been transfected, transformed or transduced with exogenous nucleic acid (transgene). The host cell includes the primary subject cell and its progeny. Exogenous nucleic acids encoding at least a portion of any of the light chain, heavy chain or anti-LAG3 antibodies described herein can be introduced into a host cell. Expression vectors comprising at least a portion of any of the light chain, heavy chain or anti-LAG3 antibodies described herein can be introduced into a host cell, and the host cell can express polypeptides comprising at least a portion of the light chain, heavy chain or anti-LAG3 antibody.

The terms "host cell" or "or a population of host cells" or related terms as used herein refer to a cell (or a population thereof) into which foreign (exogenous or transgene) nucleic acids have been introduced. The foreign nucleic acids can include an expression vector operably linked to a transgene, and the host cell can be used to express the nucleic acid and/or polypeptide encoded by the foreign nucleic acid (transgene). A host cell (or a population thereof) can be a cultured cell or can be extracted from a subject. The host cell (or a population thereof) includes the primary subject cell and its progeny without any regard for the number of passages. Progeny cells may or may not harbor identical genetic material compared to the parent cell. Host cells encompass progeny cells. In one embodiment, a host cell describes any cell (including its progeny) that has been modified, transfected, transduced, transformed, and/or manipulated in any way to express an antibody, as disclosed herein. In one example, the host cell (or population thereof) can be introduced with an expression vector operably linked to a nucleic acid encoding the desired antibody, or an antigen binding portion thereof, described herein. Host cells and populations thereof can harbor an expression vector that is stably integrated into the host's genome or can harbor an extrachromosomal expression vector. In one embodiment, host cells and populations thereof can harbor an extrachromosomal vector that is present after several cell divisions or is present transiently and is lost after several cell divisions.

Transgenic host cells can be prepared using non-viral methods, including well-known designer nucleases including zinc finger nucleases, TALENS or CRISPR/Cas. A transgene can be introduced into a host cell's genome using genome editing technologies such as zinc finger nuclease. A zinc finger nuclease includes a pair of chimeric proteins each containing a non-specific endonuclease domain of a restriction endonuclease (e.g., FokI) fused to a DNA-binding domain from an engineered zinc finger motif. The DNA-binding domain can be engineered to bind a specific sequence in the host's genome and the endonuclease domain makes a double-stranded cut. The donor DNA carries the transgene, for example any of the nucleic acids encoding a CAR or DAR construct described herein, and flanking sequences that are homologous to the regions on either side of the intended insertion site in the host cell's genome. The host cell's DNA repair machinery enables precise insertion of the transgene by homologous DNA repair. Transgenic mammalian host cells have been prepared using zinc finger nucleases (U.S. Pat. Nos. 9,597,357, 9,616,090, 9,816,074 and 8,945,868). A transgenic host cell can be prepared using TALEN (Transcription Activator-Like Effector Nucleases) which are similar to zinc finger nucleases in that they include a non-specific endonuclease domain fused to a DNA-binding domain which can deliver precise transgene insertion. Like zinc finger nucleases, TALEN also introduce a double-strand cut into the host's DNA. Transgenic host cells can be prepared using CRISPR (Clustered Regularly Interspaced Short Palindromic Repeats). CRISPR employs a Cas endonuclease coupled to a guide RNA for target specific donor DNA integration. The guide RNA includes a conserved multi-nucleotide containing protospacer adjacent motif (PAM) sequence upstream of the gRNA-binding region in the target DNA and hybridizes to the host cell target site where the Cas endonuclease cleaves the double-stranded target DNA. The guide RNA can be designed to hybridize to a specific target site. Similar to zinc finger nuclease and TALEN, the CRISPR/Cas system can be used to introduce site specific insertion of donor DNA having flanking sequences that have homology to the insertion site.

Examples of CRISPR/Cas systems used to modify genomes are described for example in U.S. Pat. Nos. 8,697,359, 10,000,772, 9,790,490, and U.S. Patent Application Publication No. US 2018/0346927. In one embodiment, transgenic host cells can be prepared using zinc finger nuclease, TALEN or CRISPR/Cas system, and the host target site can be a TRAC gene (T Cell Receptor Alpha Constant). The donor DNA can include for example any of the nucleic acids encoding a CAR or DAR construct described herein. Electroporation, nucleofection or lipofection can be used to co-deliver into the host cell the donor DNA with the zinc finger nuclease, TALEN or CRISPR/Cas system.

A host cell can be a prokaryote, for example, *E. coli*, or it can be a eukaryote, for example, a single-celled eukaryote (e.g., a yeast or other fungus), a plant cell (e.g., a tobacco or tomato plant cell), an mammalian cell (e.g., a human cell, a monkey cell, a hamster cell, a rat cell, a mouse cell, or an insect cell) or a hybridoma. In one embodiment, a host cell can be introduced with an expression vector operably linked to a nucleic acid encoding a desired antibody thereby generating a transfected/transformed host cell which is cultured under conditions suitable for expression of the antibody by the transfected/transformed host cell, and optionally recovering the antibody from the transfected/transformed host cells (e.g., recovery from host cell lysate) or recovery from the culture medium. In one embodiment, host cells comprise non-human cells including CHO, BHK, NS0, SP2/0, and YB2/0. In one embodiment, host cells comprise human cells including HEK293, HT-1080, Huh-7 and PER.C6. Examples of host cells include the COS-7 line of monkey kidney cells (ATCC CRL 1651) (see Gluzman et al., 1981, Cell 23: 175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B 11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo 205 cells, other transformed primate cell lines, normal diploid cells, cell strains derived from in vitro culture of primary tissue, primary explants, HL-60, U937, HaK or Jurkat cells. In one embodiment, host cells include lymphoid cells such as Y0, NS0 or Sp20. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "transgenic host cell" or "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

A host cell, or a population of host cells, harboring a vector (e.g., an expression vector) operably linked to a nucleic acid encoding the antibody light chains, antibody heavy chains, anti-LAG3 antibodies or antigen-binding portions thereof, are described herein. In one embodiment, a host cell harbors a vector operably linked a nucleic acid encoding a heavy chain variable region comprising at least 95% sequence identity to the amino acid sequence of SEQ ID NO:4, 6, 8 or 10. In one embodiment, nucleic acids encode a light chain variable region comprising at least 95% sequence identity to the amino acid sequence of SEQ ID NO:5, 7, 9 or 11.

Polypeptides of the present disclosure (e.g., antibodies and antigen binding proteins) can be produced using any methods known in the art. In one example, the polypeptides are produced by recombinant nucleic acid methods by inserting a nucleic acid sequence (e.g., DNA) encoding the polypeptide into a recombinant expression vector which is introduced into a host cell and expressed by the host cell under conditions promoting expression.

General techniques for recombinant nucleic acid manipulations are described for example in Sambrook et al., in *Molecular Cloning: A Laboratory Manual*, Vols. 1-3, Cold Spring Harbor Laboratory Press, 2 ed., 1989, or F. Ausubel et al., in Current Protocols in Molecular Biology (Green Publishing and Wiley-Interscience: New York, 1987) and periodic updates, herein incorporated by reference in their entireties. The nucleic acid (e.g., DNA) encoding the polypeptide is operably linked to an expression vector carrying one or more suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The expression vector can include an origin or replication that confers replication capabilities in the host cell. The expression vector can include a gene that confers selection to facilitate recognition of transgenic host cells (e.g., transformants).

The recombinant DNA can also encode any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, N.Y., 1985).

The expression vector construct can be introduced into the host cell using a method appropriate for the host cell. A variety of methods for introducing nucleic acids into host cells are known in the art, including, but not limited to, electroporation; transfection employing calcium chloride, rubidium chloride, calcium phosphate, DEAE-dextran, or other substances; viral transfection; non-viral transfection; microprojectile bombardment; lipofection; and infection (e.g., where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts. Any of the light chain, heavy chain or anti-LAG3 antibodies, or antigen binding protein thereof, can be expressed by transgenic host cells.

Antibodies and antigen binding proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc. Natl. Acad. Sci. USA. 2003 100(2):438-42; Sinclair et al. Protein Expr. Purif. 2002 (1):96-105; Connell N D. Curr. Opin. Biotechnol. 2001 12(5):446-9; Makrides et al. Microbiol. Rev. 1996 60(3):512-38; and Sharp et al. Yeast. 1991 7(7):657-78.

Antibodies and antigen binding proteins described herein can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

Antibodies and antigen binding proteins described herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified antibodies and antigen binding proteins described herein are preferably at least 65% pure, at least 75% pure, at least 85% pure, more preferably at least 95% pure, and most preferably at least 98% pure. Regardless of the exact numerical value of the purity, the polypeptide is sufficiently pure for use as a pharmaceutical product. Any of the light chain, heavy chain or anti-LAG3 antibodies, or antigen binding protein thereof, described herein can be expressed by transgenic host cells and then purified to about 65-98% purity or high level of purity using any art-known method.

In certain embodiments, the antibodies and antigen binding proteins herein can further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogenicity of the protein. See Raju et al. Biochemistry. 2001 31; 40(30):8868-76.

In one embodiment, the antibodies and antigen binding proteins described herein can be modified to become soluble polypeptides which comprises linking the Antibodies and antigen binding proteins to non-proteinaceous polymers. In one embodiment, the non-proteinaceous polymer comprises polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X—O(CH_2CH_2O)_n—CH_2CH_2OH$ (1), where n is 20 to 2300 and X is H or a terminal modification, e.g., a $C_{1-4}$ alkyl. In one embodiment, the PEG terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., Bioconjugate Chem. 6 (1995) 62-69).

The serum clearance rate of PEG-modified polypeptide may be modulated (e.g., increased or decreased) by about 10%, 20%, 30%, 40%, 50%, 60%, 70%, 80%, or even 90%, relative to the clearance rate of the unmodified antibodies and antigen binding proteins binding polypeptides. The PEG-modified antibodies and antigen binding proteins may have a half-life ($t_{1/2}$) which is enhanced relative to the half-life of the unmodified polypeptide. The half-life of PEG-modified polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified antibodies and antigen binding proteins. In some embodiments, the protein half-life is determined in vitro, such as in a buffered saline solution or in serum. In other embodiments, the protein half-life is an in vivo half-life, such as the half-life of the protein in the serum or other bodily fluid of an animal.

The present disclosure provides therapeutic compositions comprising any of the light chain, heavy chain or anti-LAG3 antibodies, or antigen binding protein thereof, described herein in and a pharmaceutically-acceptable excipient. An excipient encompasses carriers, stabilizers and excipients. Excipients of pharmaceutically acceptable excipients includes for example inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc). Additional examples include buffering agents, stabilizing agents, preservatives, non-ionic detergents, anti-oxidants and isotonifiers.

Therapeutic compositions and methods for preparing them are well known in the art and are found, for example, in "Remington: The Science and Practice of Pharmacy" (20th ed., ed. A. R. Gennaro A R., 2000, Lippincott Williams & Wilkins, Philadelphia, Pa.). Therapeutic compositions can be formulated for parenteral administration may, and can for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the antibody (or antigen binding protein thereof) described herein. Nanoparticulate formulations (e.g., biodegradable nanoparticles, solid lipid nanoparticles, liposomes) may be used to control the biodistribution of the antibody (or antigen binding protein thereof). Other potentially useful parenteral delivery systems include ethylene-vinyl acetate copolymer particles, osmotic pumps, implantable infusion systems, and liposomes. The concentration of the antibody (or antigen binding protein thereof) in the formulation varies depending upon a number of factors, including the dosage of the drug to be administered, and the route of administration.

Any of the anti-LAG3 antibodies (or antigen binding portions thereof) may be administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the antibody (or antigen binding portions thereof) is formulated in the presence of sodium acetate to increase thermal stability.

Any of the anti-LAG3 antibodies (or antigen binding portions thereof) may be formulated for oral use include tablets containing the active ingredient(s) in a mixture with non-toxic pharmaceutically acceptable excipients. Formulations for oral use may also be provided as chewable tablets, or as hard gelatin capsules wherein the active ingredient is mixed with an inert solid diluent, or as soft gelatin capsules wherein the active ingredient is mixed with water or an oil medium.

The term "subject" as used herein refers to human and non-human animals, including vertebrates, mammals and non-mammals. In one embodiment, the subject can be human, non-human primates, simian, ape, murine (e.g., mice and rats), bovine, porcine, equine, canine, feline, caprine, lupine, ranine or piscine.

The term "administering", "administered" and grammatical variants refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods. Any of the anti-LAG3 antibodies described herein (or antigen binding protein thereof) can be administered to a subject using art-known methods and delivery routes.

The terms "effective amount", "therapeutically effective amount" or "effective dose" or related terms may be used interchangeably and refer to an amount of antibody or an antigen binding protein (e.g., any of the anti-LAG3 antibodies described herein or antigen binding protein thereof) that when administered to a subject, is sufficient to effect a measurable improvement or prevention of a disease or disorder associated with tumor or cancer antigen expression. Therapeutically effective amounts of antibodies provided herein, when used alone or in combination, will vary depending upon the relative activity of the antibodies and combinations (e.g., in inhibiting cell growth) and depending upon the subject and disease condition being treated, the weight and age and sex of the subject, the severity of the disease condition in the subject, the manner of administration and the like, which can readily be determined by one of ordinary skill in the art.

In one embodiment, a therapeutically effective amount will depend on certain aspects of the subject to be treated and the disorder to be treated and may be ascertained by one skilled in the art using known techniques. In general, the polypeptide is administered at about 0.01 g/kg to about 50 mg/kg per day, preferably 0.01 mg/kg to about 30 mg/kg per day, most preferably 0.1 mg/kg to about 20 mg/kg per day. The polypeptide may be administered daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary.

The present disclosure provides methods for treating a subject having a disease associated with expression of LAG3. The disease comprises cancer or tumor cells expressing the tumor-associated antigens. In one embodiment, the cancer or tumor includes cancer of the prostate, breast, ovary, head and neck, bladder, skin, colorectal, anus, rectum, pancreas, lung (including non-small cell lung and small cell lung cancers), leiomyoma, brain, glioma, glioblastoma, esophagus, liver, kidney, stomach, colon, cervix, uterus, endometrium, vulva, larynx, vagina, bone, nasal cavity, paranasal sinus, nasopharynx, oral cavity, oropharynx, larynx, hypolarynx, salivary glands, ureter, urethra, penis and testis.

In one embodiment, the cancer comprises hematological cancers, including leukemias, lymphomas, myelomas and B cell lymphomas. Hematologic cancers include multiple myeloma (MM), non-Hodgkin's lymphoma (NHL) including Burkitt's lymphoma (BL), B chronic lymphocytic leukemia (B-CLL), systemic lupus erythematosus (SLE), B and T acute lymphocytic leukemia (ALL), acute myeloid leukemia (AML), chronic lymphocytic leukemia (CLL), diffuse large B cell lymphoma, chronic myelogenous leukemia (CML), hairy cell leukemia (HCL), follicular lymphoma, Waldenstrom's Macroglobulinemia, mantle cell lymphoma, Hodgkin's Lymphoma (HL), plasma cell myeloma, precursor B cell lymphoblastic leukemia/lymphoma, plasmacytoma, giant cell myeloma, plasma cell myeloma, heavy-chain myeloma, light chain or Bence-Jones myeloma, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, and monoclonal gammopathy of undetermined significance.

The present disclosure provides engineered LAG3 binding proteins, particularly anti-LAG3 antibodies, or antigen-binding portions thereof, that specifically bind LAG3 and uses thereof. The anti-LAG3 antibodies exhibit improved characteristics, where the improved characteristics include improved binding to LAG3 antigen, improved binding to LAG3-expressing cells and/or higher levels of cytokine release activity. The anti-LAG3 antibodies can cross-react (bind) with cynomolgus and/or mouse LAG3 antigen.

The present disclosure provides fully human anti-LAG3 antibodies and fragments thereof, that they can act as immune checkpoint inhibitors and may be used in immunotherapy for treating disorders such as cancer.

In some embodiments, the present disclosure provides an antigen-binding protein, such as a fully human antibody of an IgG class, that binds to an epitope of a LAG3 polypeptide (e.g., target antigen) or fragment of a LAG3 polypeptide. In one embodiment, the LAG3 target antigen comprises a polypeptide having a wild-type or polymorphic or mutant amino acid sequence. In one embodiment, the LAG3 target antigen comprises a human LAG3 polypeptide (UniProtKB P18627; SEQ ID NO:1), cynomolgus monkey LAG3 polypeptide (NCBI accession No. XP 005570011.1; SEQ ID NO:2), or mouse LAG3 polypeptide (UniProtKB Q61790; SEQ ID NO:3), or a fragment of any of these LAG3 polypeptides shown in FIG. 1. The LAG3 target antigen can be prepared by recombinant methods or can be chemically synthesized. The LAG3 target antigen can be in soluble form or membrane-bound form (e.g., expressed by a cell or phage). In one embodiment, the LAG3 target antigen comprises an extracellular portion of a cell surface LAG3 antigen. In one embodiment, the LAG3 target antigen is expressed by a cell, for example a cancer or non-cancer cell line that naturally expresses LAG3, or expressed by a cell line that is engineered to express LAG3 such as CHO, HeLa, HEK293, Jurkat or Panoply™ (from Creative Biogene, Shirley, N.Y.). Cell lines that do not naturally express LAG3 are not expected to bind an anti-LAG3 antibody. The LAG3 target antigen can be a fusion protein or conjugated for example with a detectable moiety such as a fluorophore. The LAG3 target antigen can be a recombinant polypeptide with or without an affinity tag such as a histidine-tag. The LAG3 target antigen can be a biotinylated LAG3 protein from human, mouse or cynomolgus (e.g., catalogue Nos. LA3-H82Fb, biotinylated human LAG3 protein from AcroBiosystems).

In one embodiment, wild type and/or mutated human LAG3 antigen can be used in an assay comparing binding capabilities of any of the anti-LAG3 antibodies described herein and/or in an epitope mapping assay.

The present disclosure provides an antigen-binding protein, such as a fully human antibody of an IgG class, wherein the antibody binds an epitope of a LAG3 polypeptide (target antigen), wherein the antibody comprises a heavy chain variable region having at least 95% sequence identity, or at least 96% sequence identity, or at least 97% sequence identity, or at least 98% sequence identity, or at least 99% sequence identity to the amino acid sequence of SEQ ID NO:4, 6 8 or 10, or combinations thereof, and the anti-LAG3 antibody comprises a light chain variable region having 95% sequence identity, or at least 96% sequence identity, or at least 97% sequence identity, or at least 98% sequence identity, or at least 99% sequence identity to the amino acid sequence of SEQ ID NO:5, 7, 9 or 11, or combinations thereof. The amino acid sequences of the heavy chain variable region and light chain variable region of antibodies 1C5-3A6, 2D12-2E3-N102D, 5C8 and 8D9, are shown in FIG. 2.

The present disclosure provides an antigen-binding protein, such as a fully human antibody of an IgG class, wherein the antibody binds an epitope of a LAG3 polypeptide (target antigen), wherein the antibody comprises a heavy chain variable region having at least 95% sequence identity, or at least 96% sequence identity, or at least 97% sequence identity, or at least 98% sequence identity, or at least 99% sequence identity to the amino acid sequence of SEQ ID NO:4, 6 8 or 10, or combinations thereof.

The present disclosure provides an antigen-binding protein, such as a fully human antibody of an IgG class, wherein the antibody binds an epitope of a LAG3 polypeptide (target antigen), wherein the antibody comprises a light chain variable region having 95% sequence identity, or at least 96% sequence identity, or at least 97% sequence identity, or at least 98% sequence identity, or at least 99% sequence identity to the amino acid sequence of SEQ ID NO:5, 7, 9 or 11, or combinations thereof.

In one embodiment, the anti-LAG3 antibody is an isolated antibody. In one embodiment, the anti-LAG3 antibody is a recombinant antibody.

In one embodiment, the anti-LAG3 antibody comprises an IgG1, IgG2, IgG3 or IgG4 class antibody. In one embodiment, the anti-LAG3 antibody comprises an IgG1 or IgG4 class antibody. In one embodiment, the hinge region of the anti-LAG3 antibody can be mutated to alter the number of potential disulfide bond formation. In one embodiment, the anti-LAG3 antibody comprises a hinge region having the amino acid sequence CPPC, CPSC, SPPC or SPSC. In one embodiment, the anti-LAG3 antibody comprises a heavy chain constant region having a hinge region wherein the amino acid sequence CPSC, SPPC or SPSC replaces the sequence CPPC. In one embodiment, the heavy chain of the anti-LAG3 antibody can be mutated to eliminate one or more NG motifs (e.g., as part of an NGR motif) that are known to isomerize. In one embodiment, the isomerized site can bind integrin. In one embodiment, the anti-LAG3 antibody comprises a heavy chain that includes an SGR motif that replaces an NGR motif. In one embodiment, the anti-LAG3 antibody comprises a heavy chain variable region wherein an SGR motif replaces an NGR motif. In one embodiment, the heavy and/or light chain of an anti-LAG3 antibody can be mutated, and the mutated antibody exhibits the same or similar binding capabilities to LAG3 antigen and/or LAG3-expressing cells.

Figure 4:
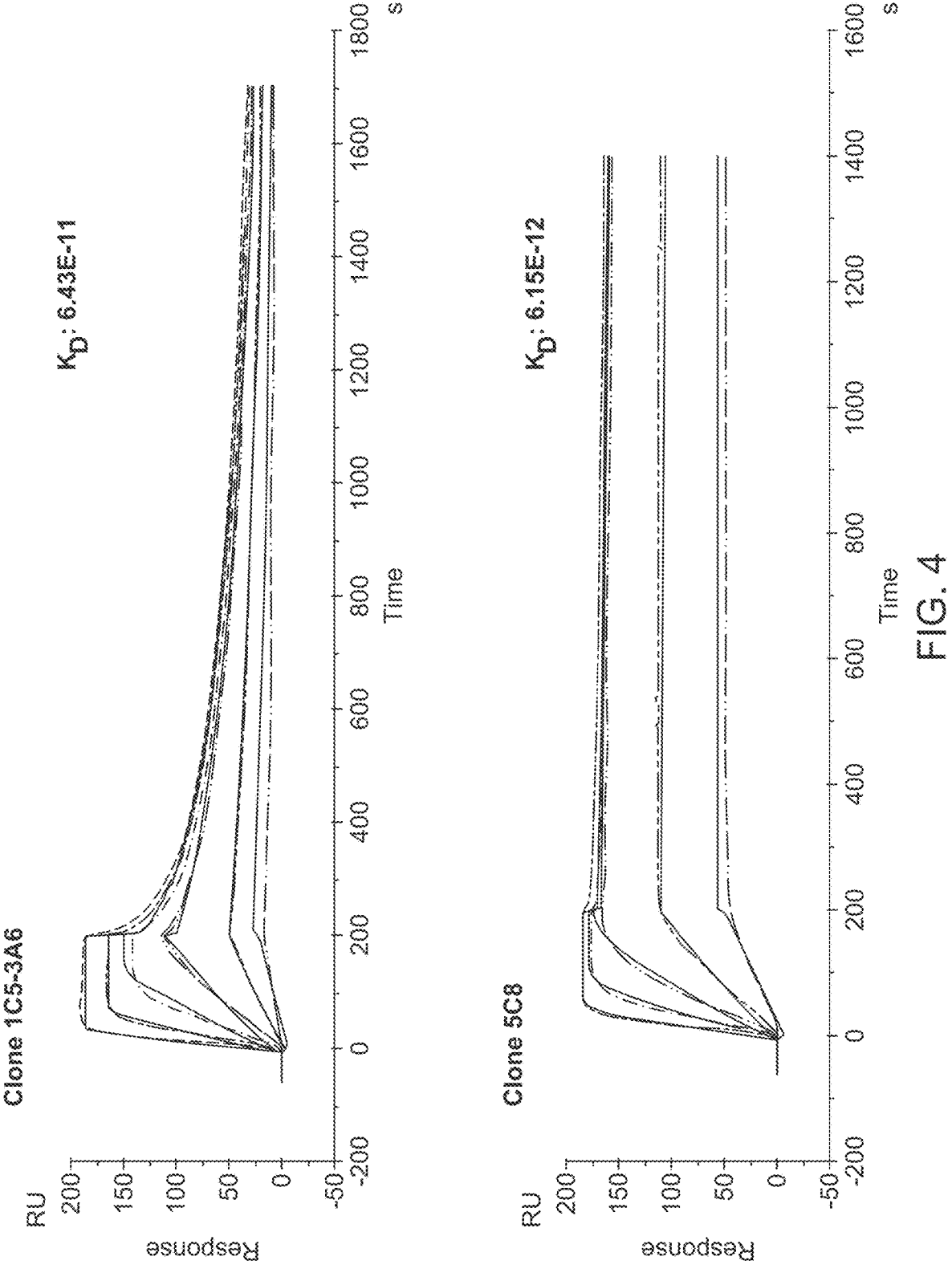
FIG. 4 shows a series of SPR sensorgrams of binding kinetics of the anti-LAG3 antibodies and their measured $K_D$ values. The Biacore experiment is described in Example 2.
Figure 4:
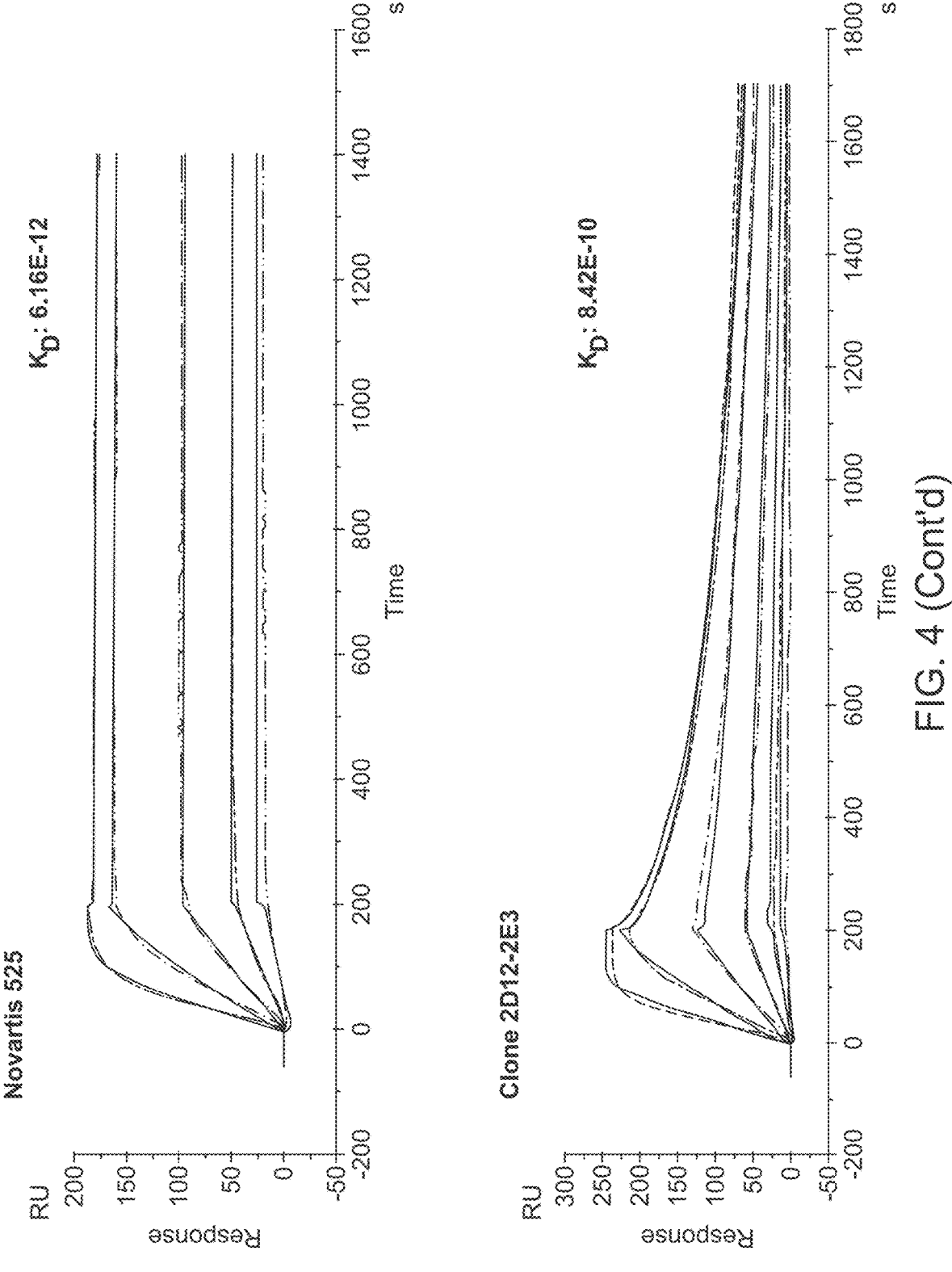
Figure 4:
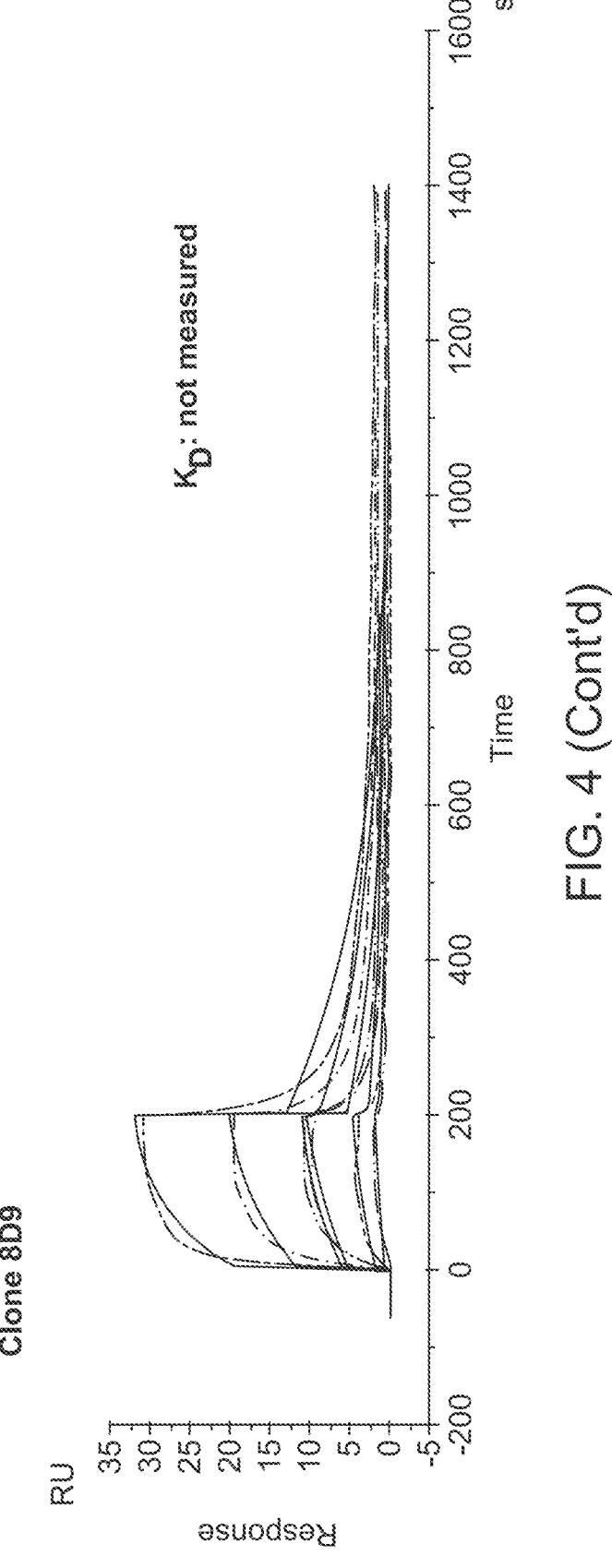

In one embodiment, the anti-LAG3 antibody, or fragment thereof, comprises an antigen binding portion that binds an epitope of a LAG3 polypeptide (target antigen) with a binding affinity ($K_D$) of $10^{-6}$ M or less, $10^{-7}$ M or less, $10^{-8}$ M or less, $10^{-9}$ M or less, or $10^{-10}$ M or less (see FIG. 4). In one embodiment, binding between the anti-LAG3 antibody, or fragment thereof, can be detected and measured using surface plasmon resonance, flow cytometry and/or ELISA.

The present disclosure provides an anti-LAG3 antibody which binds an epitope of a LAG3 polypeptide from a human, and can bind (e.g., cross-react) with an epitope of a LAG3 polypeptide (e.g., homologous antigen) from at least one of a non-human animal such as mouse, rat, goat, rabbit, hamster and/or monkey (e.g., cynomolgus). In one embodiment, the anti-LAG3 antibody binds mouse LAG3 with a binding affinity $K_D$ of $10^{-5}$ M or less, or $10^{-10}$ M or less, or $10^{-7}$ M or less, or $10^{-8}$ M or less, or $10^{-9}$ M or less, or $10^{-10}$ M or less. In one embodiment, the anti-LAG3 antibody binds cynomolgus LAG3 with a binding affinity $K_D$ of $10^{-5}$ M or less, or $10^{-6}$ M or less, or $10^{-7}$ M or less, or $10^{-8}$ M or less, or $10^{-9}$ M or less, or $10^{-10}$ M or less.

The present disclosure provides a fully human antibody that binds a LAG3 polypeptide, wherein the antibody comprises both heavy and light chains, wherein the heavy/light chain variable region amino acid sequences have at least 95% sequence identity, or at least 96% sequence identity, or at least 97% sequence identity, or at least 98% sequence identity, or at least 99% sequence identity to any of the following amino acid sequence sets: SEQ ID NOS:4 and 5 (called 1C5-3A6 herein), SEQ ID NOS:6 and 7 (called 2D12-2E3-N102D herein), SEQ ID NOS:8 and 9 (called 5C8 herein), or SEQ ID NOS:10 and 11 (called 8D9 herein). The amino acid sequences of the heavy chain variable region and light chain variable region of antibodies 1C5-3A6, 2D12-2E3-N102D, 5C8 and 8D9, are shown in FIG. 2.

The present disclosure provides a Fab fully human antibody fragment comprising a variable region from an antibody heavy chain and a variable region from an antibody light chain. In some embodiments, the sequence of the variable region from the heavy chain is at least 95% identical, or at least 96% identical, or at least 97% identical, or at least 98% identical, or at least 99% identical to the amino acid sequence of SEQ ID NO:4, 6, 8 or 10, or combinations thereof, and the sequence of the variable region from the light chain is at least 95% identical, or at least 96% identical, or at least 97% identical, or at least 98% identical, or at least 99% identical to the amino acid sequence of SEQ ID NO:5, 7, 9 or 11, or combinations thereof. In some embodiments, the sequence of the variable region from the heavy chain is at least 95% identical, or at least 96% identical, or at least 97% identical, or at least 98% identical, or at least 99% identical to the amino acid sequence of SEQ ID NO:4, 6, 8 or 10, or combinations thereof, and the sequence of the variable region from the light chain is at least 95% identical, or at least 96% identical, or at least 97% identical, or at least 98% identical, or at least 99% identical to the amino acid sequence of SEQ ID NO:5, 7, 9 or 11, or combinations thereof. The amino acid sequences of the heavy chain variable region and light chain variable region of antibodies 1C5-3A6, 2D12-2E3-N102D, 5C8 and 8D9, are shown in FIG. 2.

The present disclosure provides a Fab fully human antibody fragment comprising a heavy chain variable region and a light chain variable region, wherein the heavy/light chain variable region amino acid sequences are at least 95% identical, or at least 96% identical, or at least 97% identical, or at least 98% identical, or at least 99% identical to any of the following amino acid sequence sets: SEQ ID NOS:4 and 5 (called 1C5-3A6 herein), SEQ ID NOS:6 and 7 (called 2D12-2E3-N102D herein), SEQ ID NOS:8 and 9 (called 5C8 herein), or SEQ ID NOS:10 and 11 (called 8D9 herein).

The present disclosure provides a single chain fully human antibody comprising a polypeptide chain having a variable region from a fully human heavy chain and a variable region from a fully human light chain, and optionally a linker (e.g., peptide linker) joining the variable heavy and variable light chain regions. In some embodiments, the variable heavy region comprises at least 95% sequence identity, or at least 96% sequence identity, or at least 97% sequence identity, or at least 98% sequence identity, or at least 99% sequence identity to the amino acid sequence of SEQ ID NO:4, 6, 8 or 10, or combinations thereof, and the variable light region comprises at least 95% sequence identity, or at least 96% sequence identity, or at least 97% sequence identity, or at least 98% sequence identity, or at least 99% sequence identity to the amino acid sequence of SEQ ID NO:5, 7, 9 or 11, or combinations thereof. In some embodiments, the variable heavy region comprises at least 95% sequence identity, or at least 96% sequence identity, or at least 97% sequence identity, or at least 98% sequence identity, or at least 99% sequence identity to the amino acid sequence of SEQ ID NO:4, 6, 8 or 10, or combinations thereof, and the variable light region comprises at least 95% sequence identity, or at least 96% sequence identity, or at least 97% sequence identity, or at least 98% sequence identity, or at least 99% sequence identity to the amino acid sequence of SEQ ID NO:5, 7, 9 or 11, or combinations thereof.

The present disclosure provides a single chain fully human antibody comprising a polypeptide chain having heavy chain variable region and a light chain variable region, wherein the heavy/light chain variable region amino acid sequence sets are at least 95% identical, or at least 96% identical, or at least 97% identical, or at least 98% identical, or at least 99% identical to any of the following amino acid sequence sets: SEQ ID NOS: SEQ ID NOS:4 and 5 (called 1C5-3A6 herein), SEQ ID NOS:6 and 7 (called 2D12-2E3-N102D herein), SEQ ID NOS:8 and 9 (called 5C8 herein), or SEQ ID NOS:10 and 11 (called 8D9 herein). In one embodiment, the single chain fully human antibody comprises an optional linker (e.g., peptide linker) joining the variable heavy and variable light chain regions.

The present disclosure provides therapeutic compositions comprising any of the anti-LAG3 antibodies described herein, or antigen binding proteins thereof, and a pharmaceutically-acceptable excipient. An excipient encompasses carriers and stabilizers. In one embodiment, the therapeutic compositions comprise an anti-LAG3 antibody, or antigen binding fragment thereof, comprising a heavy chain variable region and a light chain variable region, wherein the heavy/light chain variable region amino acid sequences are at least 95% identical, or at least 96% identical, or at least 97% identical, or at least 98% identical, or at least 99% identical to any of the following amino acid sequence sets: SEQ ID NOS: SEQ ID NOS:4 and 5 (called 1C5-3A6 herein), SEQ ID NOS:6 and 7 (called 2D12-2E3-N102D herein), SEQ ID NOS:8 and 9 (called 5C8 herein), or SEQ ID NOS:10 and 11 (called 8D9 herein).

The present disclosure provides a kit, comprising any one of the disclosed fully human anti-LAG3 antibodies, or any of the antigen-binding fragments thereof, or any of the Fab fragments or single chain antibodies described herein.

The present disclosure provides a nucleic acid encoding an antibody heavy chain variable region having at least 95% sequence identity, or at least 96% sequence identity, or at least 97% sequence identity, or at least 98% sequence identity, or at least 99% sequence identity to the amino acid sequence of SEQ ID NO:4, 6, 8 or 10, or combinations thereof. The present disclosure provides a nucleic acid encoding an antibody light chain variable region having at least 95% sequence identity, or at least 96% sequence identity, or at least 97% sequence identity, or at least 98% sequence identity, or at least 99% sequence identity to the amino acid sequence of SEQ ID NO:5, 7, 9 or 11, or combinations thereof.

The present disclosure provides a first nucleic acid encoding an antibody heavy chain variable region having at least 95% sequence identity, or at least 96% sequence identity, or at least 97% sequence identity, or at least 98% sequence identity, or at least 99% sequence identity to the amino acid sequence of SEQ ID NO:4, 6, 8 or 10, or combinations thereof. The present disclosure provides a second nucleic acid encoding an antibody light chain variable region having at least 95% sequence identity, or at least 96% sequence identity, or at least 97% sequence identity, or at least 98% sequence identity, or at least 99% sequence identity to the amino acid sequence of SEQ ID NO:5, 7, 9 or 11, or combinations thereof.

The present disclosure provides a nucleic acid encoding an antibody heavy chain variable region having at least 95% sequence identity, or at least 96% sequence identity, or at least 97% sequence identity, or at least 98% sequence identity, or at least 99% sequence identity to the amino acid sequence of SEQ ID NO:4, 6, 8 or 10, or combinations thereof, and the nucleic acid encodes an antibody light chain variable region having at least 95% sequence identity, or at least 96% sequence identity, or at least 97% sequence identity, or at least 98% sequence identity, or at least 99% sequence identity to the amino acid sequence of SEQ ID NO:5, 7, 9 or 11, or combinations thereof.

The present disclosure provides a nucleic acid encoding an antibody comprising both heavy and light chains, wherein the heavy/light chain variable region amino acid sequences have at least 95% sequence identity, or at least 96% sequence identity, or at least 97% sequence identity, or at least 98% sequence identity, or at least 99% sequence identity to any of the following amino acid sequence sets: SEQ ID NOS: SEQ ID NOS:4 and 5 (called 1C5-3A6 herein), SEQ ID NOS:6 and 7 (called 2D12-2E3-N102D herein), SEQ ID NOS:8 and 9 (called 5C8 herein), or SEQ ID NOS:10 and 11 (called 8D9 herein).

The present disclosure provides a nucleic acid encoding a Fab fully human antibody fragment comprising a variable region from a heavy chain and a variable region from a light chain, wherein the amino acid sequence of the variable region from the heavy chain is at least 95% identical, or at least 96% identical, or at least 97% identical, or at least 98% identical, or at least 99% identical to the amino acid sequence of SEQ ID NO:4, 6, 8 or 10, or combinations thereof. The present disclosure provides a nucleic acid encoding a Fab fully human antibody fragment comprising a variable region from a heavy chain and a variable region from a light chain, wherein the amino acid sequence of the variable region from the light chain is at least 95% identical, or at least 96% identical, or at least 97% identical, or at least 98% identical, or at least 99% identical to the amino acid sequence of SEQ ID NO:5, 7, 9 or 11, or combinations thereof.

The present disclosure provides a first nucleic acid encoding a Fab fully human antibody fragment comprising a variable region from a heavy chain and a variable region from a light chain, wherein the amino acid sequence of the variable region from the heavy chain is at least 95% identical, or at least 96% identical, or at least 97% identical, or at least 98% identical, or at least 99% identical to the amino acid sequence of SEQ ID NO:4, 6, 8 or 10, or combinations thereof. The present disclosure provides a second nucleic acid encoding a Fab fully human antibody fragment comprising a variable region from a heavy chain and a variable region from a light chain, wherein the amino acid sequence of the variable region from the light chain is at least 95% identical, or at least 96% identical, or at least 97% identical, or at least 98% identical, or at least 99% identical to the amino acid sequence of SEQ ID NO:5, 7, 9 or 11, or combinations thereof.

The present disclosure provides a nucleic acid encoding a Fab fully human antibody fragment comprising a variable region from a heavy chain and a variable region from a light chain, wherein the amino acid sequence of the variable region from the heavy chain is at least 95% identical, or at least 96% identical, or at least 97% identical, or at least 98% identical, or at least 99% identical to the amino acid sequence of SEQ ID NO:4, 6, 8 or 10, or combinations thereof, and the nucleic acid encodes the variable region from a light chain, wherein the amino acid sequence of the variable region from the light chain is at least 95% identical, or at least 96% identical, or at least 97% identical, or at least 98% identical, or at least 99% identical to the amino acid sequence of SEQ ID NO:5, 7, 9 or 11, or combinations thereof.

The present disclosure provides a nucleic acid encoding a Fab fully human antibody fragment comprising a heavy chain variable region and a light chain variable region, wherein the heavy/light chain variable region amino acid sequences are at least 95% identical, or at least 96% identical, or at least 97% identical, or at least 98% identical, or at least 99% identical to any of the following amino acid sequence sets: SEQ ID NOS: SEQ ID NOS:4 and 5 (called 1C5-3A6 herein), SEQ ID NOS:6 and 7 (called 2D12-2E3-N102D herein), SEQ ID NOS:8 and 9 (called 5C8 herein), or SEQ ID NOS:10 and 11 (called 8D9 herein).

The present disclosure provides a nucleic acid encoding a single chain fully human antibody comprising a polypeptide chain having a variable region from a fully human heavy chain and a variable region from a fully human light chain, and optionally a linker (e.g., peptide linker) joining the variable heavy and variable light chain regions. In some embodiments, the nucleic acid encodes a variable heavy region comprises at least 95% sequence identity, or at least 96% sequence identity, or at least 97% sequence identity, or at least 98% sequence identity, or at least 99% sequence identity to the amino acid sequence of SEQ ID NO:4, 6, 8 or 10, or combinations thereof, and the nucleic acid encodes a variable light region which comprises at least 95% sequence identity, or at least 96% sequence identity, or at least 97% sequence identity, or at least 98% sequence identity, or at least 99% sequence identity to the amino acid sequence of SEQ ID NO:5, 7, 9 or 11, or combinations thereof. In one embodiment, the peptide linker comprises the amino acid sequence (GGGGS)N (SEQ ID NO:12) where N is 1-6. In one embodiment, the peptide linker comprises the amino acid sequence GGGGSGGGGSGGGGS (SEQ ID NO:13).

The present disclosure provides nucleic acids encoding a single chain fully human antibody comprising a polypeptide chain having a variable region from a fully human heavy chain and a variable region from a fully human light chain, and optionally a linker (e.g., peptide linker) joining the variable heavy and variable light chain regions. In some embodiments, the variable heavy region comprises at least 95% sequence identity, or at least 96% sequence identity, or at least 97% sequence identity, or at least 98% sequence identity, or at least 99% sequence identity to the amino acid sequence of SEQ ID NO:4, 6, 8 or 10, or combinations thereof, and the variable light region which comprises at least 95% sequence identity, or at least 96% sequence identity, or at least 97% sequence identity, or at least 98% sequence identity, or at least 99% sequence identity to the amino acid sequence of SEQ ID NO:5, 7, 9 or 11, or combinations thereof. In one embodiment, the peptide linker comprises the amino acid sequence (GGGGS)N (SEQ ID NO:12) where N is 1-6. In one embodiment, the peptide linker comprises the amino acid sequence GGGGSGGGGSGGGGS (SEQ ID NO:13).

The present disclosure provides a nucleic acid encoding a single chain fully human antibody which is a single chain antibody comprising a polypeptide chain having heavy chain variable region and a light chain variable region, wherein the heavy/light chain variable region amino acid sequence sets are at least 95% identical, or at least 96% identical, or at least 97% identical, or at least 98% identical, or at least 99% identical to any of the following amino acid sequence sets: SEQ ID NOS: SEQ ID NOS:4 and 5 (called 1C5-3A6 herein), SEQ ID NOS:6 and 7 (called 2D12-2E3-N102D herein), SEQ ID NOS:8 and 9 (called 5C8 herein), or SEQ ID NOS:10 and 11 (called 8D9 herein). In one embodiment, the nucleic acid encodes a single chain fully human antibody comprising an optional linker (e.g., peptide linker) joining the variable heavy and variable light chain regions. In one embodiment, the peptide linker comprises the amino acid sequence (GGGGS)$_N$ (SEQ ID NO:12) where N is 1-6. In one embodiment, the peptide linker comprises the amino acid sequence GGGGSGGGGSGGGGS (SEQ ID NO:13).

The present disclosure provides a first vector (e.g., a first expression vector) operably linked to a first nucleic acid encoding a heavy chain variable region comprising at least 95% sequence identity, or at least 96% sequence identity, or at least 97% sequence identity, or at least 98% sequence identity, or at least 99% sequence identity to the amino acid sequence of SEQ ID NO:4, 6, 8 or 10, and a second vector (e.g., second expression vector) operably linked to a second nucleic acid encoding a light chain variable region comprising at least 95% sequence identity, or at least 96% sequence identity, or at least 97% sequence identity, or at least 98% sequence identity, or at least 99% sequence identity to sequence identity to the amino acid sequence of SEQ ID NO:5, 7, 9 or 11.

The present disclosure provides a first vector (e.g., a first expression vector) operably linked to a first nucleic acid encoding a heavy chain variable region comprising at least 95% sequence identity, or at least 96% sequence identity, or at least 97% sequence identity, or at least 98% sequence identity, or at least 99% sequence identity to the amino acid sequence of SEQ ID NO:4, 6, 8 or 10. In one embodiment, the first vector is also operably linked to a second nucleic acid encoding a light chain variable region comprising at least 95% sequence identity, or at least 96% sequence identity, or at least 97% sequence identity, or at least 98% sequence identity, or at least 99% sequence identity to the amino acid sequence of SEQ ID NO:5, 7, 9 or 11.

The present disclosure provides a vector (e.g., an expression vector) operably linked to nucleic acids encoding a heavy chain variable region and a light chain variable region having at least 95% sequence identity, or at least 96% sequence identity, or at least 97% sequence identity, or at least 98% sequence identity, or at least 99% sequence identity to any of the following amino acid sequence sets: SEQ ID NOS: SEQ ID NOS:4 and 5 (called 1C5-3A6 herein), SEQ ID NOS:6 and 7 (called 2D12-2E3-N102D herein), SEQ ID NOS:8 and 9 (called 5C8 herein), or SEQ ID NOS:10 and 11 (called 8D9 herein).

The present disclosure provides a first vector (e.g., a first expression vector) operably linked to a first nucleic acid encoding a Fab fully human antibody fragment comprising a heavy chain variable region comprising at least 95% sequence identity, or at least 96% sequence identity, or at least 97% sequence identity, or at least 98% sequence identity, or at least 99% sequence identity to the amino acid sequence of SEQ ID NO:4, 6, 8 or 10. The present disclosure also provides a second vector (e.g., a second expression vector) operably linked to a second nucleic acid encoding a Fab fully human antibody fragment comprising a light chain variable region comprising at least 95% sequence identity, or at least 96% sequence identity, or at least 97% sequence identity, or at least 98% sequence identity, or at least 99% sequence identity to the amino acid sequence of SEQ ID NO:5, 7, 9 or 11.

The present disclosure provides a first vector (e.g., a first expression vector) operably linked to a first nucleic acid encoding a Fab fully human antibody fragment comprising a heavy chain variable region comprising at least 95% sequence identity, or at least 96% sequence identity, or at least 97% sequence identity, or at least 98% sequence identity, or at least 99% sequence identity to the amino acid sequence of SEQ ID NO:4, 6, 8 or 10. In one embodiment, the first vector is also operably linked to a second nucleic acid encoding a light chain variable region comprising at least 95% sequence identity, or at least 96% sequence identity, or at least 97% sequence identity, or at least 98% sequence identity, or at least 99% sequence identity to the amino acid sequence of SEQ ID NO:5, 7, 9 or 11.

The present disclosure provides a vector (e.g., an expression vector) operably linked to nucleic acids encoding a Fab fully human antibody fragment comprising a heavy chain variable region and a light chain variable region having at least 95% sequence identity, or at least 96% sequence identity, or at least 97% sequence identity, or at least 98% sequence identity, or at least 99% sequence identity to any of the following amino acid sequence sets: SEQ ID NOS: SEQ ID NOS:4 and 5 (called 1C5-3A6 herein), SEQ ID NOS:6 and 7 (called 2D12-2E3-N102D herein), SEQ ID NOS:8 and 9 (called 5C8 herein), or SEQ ID NOS:10 and 11 (called 8D9 herein).

The present disclosure provides a first vector (e.g., a first expression vector) operably linked to a nucleic acid encoding a single chain fully human antibody comprising a polypeptide chain having a variable region from a fully human heavy chain and a variable region from a fully human light chain, and optionally a linker (e.g., peptide linker) joining the variable heavy and variable light chain regions, wherein the variable heavy region comprises at least 95% sequence identity, or at least 96% sequence identity, or at least 97% sequence identity, or at least 98% sequence identity, or at least 99% sequence identity to the amino acid sequence of SEQ ID NO:4, 6, 8 or 10, or combinations thereof, and wherein the variable light region comprises at least 95% sequence identity, or at least 96% sequence identity, or at least 97% sequence identity, or at least 98% sequence identity, or at least 99% sequence identity to the amino acid sequence of SEQ ID NO:5, 7, 9 or 11, or combinations thereof. In one embodiment, the peptide linker comprises the amino acid sequence (GGGGS)N (SEQ ID NO:12) where N is 1-6. In one embodiment, the peptide linker comprises the amino acid sequence GGGGSGGGGSGGGGS (SEQ ID NO:13).

The present disclosure provides a first vector (e.g., a first expression vector) operably linked to a nucleic acid encoding a single chain fully human antibody comprising a polypeptide chain having a variable region from a fully human heavy chain and a variable region from a fully human light chain, and optionally a linker (e.g., peptide linker) joining the variable heavy and variable light chain regions, wherein the variable heavy region comprises at least 95% sequence identity, or at least 96% sequence identity, or at least 97% sequence identity, or at least 98% sequence identity, or at least 99% sequence identity to any of the following amino acid sequence sets: SEQ ID NOS: SEQ ID NOS:4 and 5 (called 1C5-3A6 herein), SEQ ID NOS:6 and 7 (called 2D12-2E3-N102D herein), SEQ ID NOS:8 and 9 (called 5C8 herein), or SEQ ID NOS:10 and 11 (called 8D9 herein). In one embodiment, the peptide linker comprises the amino acid sequence (GGGGS)N (SEQ ID NO:12) where N is 1-6. In one embodiment, the peptide linker comprises the amino acid sequence GGGGSGGGGSGGGGS (SEQ ID NO:13).

The present disclosure provides a host cell, or a population of host cells, wherein the host cell or individual host cells from the population of host cells harbors a first vector (e.g., a first expression vector) operably linked to a first nucleic acid encoding a heavy chain variable region comprising at least 95% sequence identity to the amino acid sequence of SEQ ID NO:4, 6, 8 or 10, and the host cell or individual host cells from the population of host cells harbors a second vector (e.g., a second expression vector) operably linked to a second nucleic acid encoding a light chain variable region comprising at least 95% sequence identity to the amino acid sequence of SEQ ID NO:5, 7, 9 or 11. In one embodiment, the first expression vector directs expression of the heavy chain variable region and the second expression vector directs expression of the light chain variable region in the host cell or the population of host cells.

The present disclosure provides a first host cell, or a first population of host cells, wherein the first host cell or individual host cells from the first population of host cells harbors a first vector (e.g., a first expression vector) operably linked to a first nucleic acid encoding a heavy chain variable region comprising at least 95% sequence identity to the amino acid sequence of SEQ ID NO:4, 6, 8 or 10, and a second host cell or a second population of host cells, wherein the second host cell or individual host cells from the second population of host cells harbors a second vector (e.g., a first expression vector) operably linked to a second nucleic acid encoding a light chain variable region comprising at least 95% sequence identity to the amino acid sequence of SEQ ID NO:5, 7, 9 or 11. In one embodiment, the first expression vector directs expression of the heavy chain variable region in the first host cell, and the second expression vector directs expression of the light chain variable region in the second host cell.

The present disclosure provides a host cell, or a population of host cells, wherein the host cell or individual host cells from the population of host cells harbors a vector (e.g., an expression vector) operably linked to a first nucleic acid encoding a heavy chain variable region comprising at least 95% sequence identity to the amino acid sequence of SEQ ID NO:4, 6, 8 or 10, and the vector in the host cell is also operably linked to a second nucleic acid encoding a light chain variable region comprising at least 95% sequence identity to the amino acid sequence of SEQ ID NO:5, 7, 9 or 11. In one embodiment, the expression vector directs expression of the heavy chain variable region and the light chain variable region in the host cell.

The present disclosure provides a host cell, or a population of host cells, wherein the host cell or individual host cells from the population of host cells harbors a first vector (e.g., a first expression vector) operably linked to a first nucleic acid encoding a Fab fully human antibody fragment comprising a variable region from a heavy chain, wherein the amino acid sequence of the variable region from the heavy chain is at least 95% identical to the amino acid sequence of SEQ ID NO:4, 6, 8 or 10, or combinations thereof. In one embodiment, the host cell or individual host cells from the population of host cells harbors also harbors a second vector (e.g., a second expression vector) operably linked to a second nucleic acid encoding a variable region from a light chain, wherein the amino acid sequence of the variable region from the light chain is at least 95% identical to the amino acid sequence of SEQ ID NO:5, 7, 9 or 11, or combinations thereof. In one embodiment, the first expression vector directs expression of the heavy chain variable region and the second expression vector directs expression of the light chain variable region in the host cell.

The present disclosure provides a first host cell, or a first population of host cells, wherein the first host cell or individual host cells from the first population of host cells harbors a first vector (e.g., a first expression vector) operably linked to a first nucleic acid encoding a Fab fully human antibody fragment comprising a variable region from a heavy chain, wherein the amino acid sequence of the variable region from the heavy chain is at least 95% identical to the amino acid sequence of SEQ ID NO:4, 6, 8 or 10, or combinations thereof. The present disclosure also provides a second host cell or a second population of host cells, wherein the second host cell or individual host cells from the second population of host cells harbors a second vector (e.g., a second expression vector) operably linked to a second nucleic acid encoding a variable region from a light chain, wherein the amino acid sequence of the variable region from the light chain is at least 95% identical to the amino acid sequence of SEQ ID NO:5, 7, 9 or 11, or combinations thereof. In one embodiment, the first expression vector directs expression of the heavy chain variable region in the first host cell, and the second expression vector directs expression of the light chain variable region in the second host cell.

The present disclosure provides a host cell, or a population of host cells, wherein the host cell or individual host cells from the population of host cells harbors a vector (e.g., an expression vector) operably linked to a first nucleic acid encoding a Fab fully human antibody fragment comprising a comprising a variable region from a heavy chain, wherein the amino acid sequence of the variable region from the heavy chain is at least 95% identical to the amino acid sequence of SEQ ID NO:4, 6, 8 or 10, or combinations thereof, and the vector in the host cell is also operably linked to a second nucleic acid encoding a light chain variable region, wherein the amino acid sequence of the variable region from the light chain is at least 95% identical to the amino acid sequence of SEQ ID NO:5, 7, 9 or 11, or combinations thereof. In one embodiment, the expression vector directs expression of the heavy chain variable region and the light chain variable region in the host cell.

The present disclosure provides a host cell, or a population of host cells, wherein the host cell or individual host cells from the population of host cells harbors a first vector (e.g., a first expression vector) operably linked to a nucleic acid encoding a single chain fully human antibody comprising a polypeptide chain having a variable region from a fully human heavy chain and a variable region from a fully human light chain, and optionally a linker (e.g., peptide linker) joining the variable heavy and variable light chain regions, wherein the variable heavy region comprises at least 95% sequence identity to the amino acid sequence of SEQ ID NO:4, 6, 8 or 10, or combinations thereof, and wherein the variable light region comprises at least 95% sequence identity to the amino acid sequence of SEQ ID NO:5, 7, 9 or 11, or combinations thereof. In one embodiment, the first vector include a nucleic acid sequence encoding a peptide linker comprising the amino acid sequence (GGGGS)N (SEQ ID NO:12) where N is 1-6. In one embodiment, the peptide linker comprises the amino acid sequence GGGGSGGGGSGGGGS (SEQ ID NO:13). In one embodiment, the expression vector directs expression of the single chain antibody in the host cell.

The present disclosure provides a method for preparing a first polypeptide having an antibody heavy chain variable region, the method comprising: culturing a population (e.g., a plurality) of the first host cells harboring the first expression vector under conditions suitable for expressing the first polypeptide having the antibody heavy chain variable region having at least 95% sequence identity to the amino acid sequence of SEQ ID NO:4, 6, 8 or 10. In one embodiment, the method further comprises: recovering from the population of the first host cells the expressed first polypeptide having at least 95% sequence identity to the amino acid sequence of SEQ ID NO:4, 6, 8 or 10.

The present disclosure provides a method for preparing a second polypeptide having an antibody light chain variable region, the method comprising: culturing a population (e.g., a plurality) of the second host cells harboring the second expression vector under conditions suitable for expressing the second polypeptide having the antibody light chain variable region having at least 95% sequence identity to the amino acid sequence of SEQ ID NO:5, 7, 9 or 11. In one embodiment, the method further comprises: recovering from the population of the second host cells the expressed second polypeptide having at least 95% sequence identity to the amino acid sequence of SEQ ID NO:5, 7, 9 or 11.

The present disclosure provides a method for preparing a first polypeptide having an antibody heavy chain variable region, and for preparing the second polypeptide having an antibody light chain variable region, the method comprising: culturing a population (e.g., a plurality) of the host cells harboring the first expression vector (which is operably linked to the first nucleic acid encoding the first polypeptide) and second expression vector (which is operably linked to the second nucleic acid encoding the second polypeptide) under conditions suitable for expressing the first polypeptide having the antibody heavy chain variable region having at least 95% sequence identity to the amino acid sequence of SEQ ID NO:4, 6, 8 or 10, and suitable for expressing the second polypeptide having the antibody light chain variable region having at least 95% sequence identity to the amino acid sequence of SEQ ID NO:5, 7, 9 or 11. In one embodiment, the method further comprises: recovering from the population of the host cells the expressed first polypeptide having at least 95% sequence identity to the amino acid sequence of SEQ ID NO:4, 6, 8 or 10, and recovering from the population of the host cells the expressed second polypeptide having at least 95% sequence identity to the amino acid sequence of SEQ ID NO:5, 7, 9 or 11.

The present disclosure provides a method for preparing a first polypeptide having an antibody heavy chain variable region, the method comprising: culturing a population (e.g., a plurality) of the first host cells harboring the first expression vector under conditions suitable for expressing the first polypeptide having the antibody heavy chain variable region having at least 95% sequence identity to the amino acid sequence of SEQ ID NO:4, 6, 8 or 10. In one embodiment, the method further comprises: recovering from the population of the first host cells the expressed first polypeptide having at least 95% sequence identity to the amino acid sequence of SEQ ID NO:4, 6, 8 or 10.

The present disclosure provides a method for preparing a second polypeptide having an antibody light chain variable region, the method comprising: culturing a population (e.g., a plurality) of the second host cells harboring the second expression vector under conditions suitable for expressing the second polypeptide having the antibody light chain variable region having at least 95% sequence identity to the amino acid sequence of SEQ ID NO:5, 7, 9 or 11. In one embodiment, the method further comprises: recovering from the population of the second host cells the expressed second polypeptide having at least 95% sequence identity to the amino acid sequence of SEQ ID NO:5, 7, 9 or 11.

The present disclosure provides a method for preparing a first polypeptide having an antibody heavy chain variable region, and for preparing the second polypeptide having an antibody light chain variable region, the method comprising: culturing a population (e.g., a plurality) of the host cells harboring the expression vector (which is operably linked to the first nucleic acids encoding the first polypeptide and operably linked to the second nucleic acid encoding the second polypeptide) under conditions suitable for expressing the first polypeptide having the antibody heavy chain variable region having at least 95% sequence identity to the amino acid sequence of SEQ ID NO:4, 6, 8 or 10, and suitable for expressing the second polypeptide having the antibody light chain variable region having at least 95% sequence identity to the amino acid sequence of SEQ ID NO:5, 7, 9 or 11. In one embodiment, the method further comprises: recovering from the population of the host cells the expressed first polypeptide having at least 95% sequence identity to the amino acid sequence of SEQ ID NO:4, 6, 8 or 10, and recovering from the population of the host cells the expressed second polypeptide having at least 95% sequence identity to the amino acid sequence of SEQ ID NO:5, 7, 9 or 11.

The present disclosure provides a method for treating a subject having a disease associated with LAG3 over-expression or LAG3 mal-expression, the method comprising: administering to the subject an effective amount of a therapeutic composition comprising any one or any combination of 2-3 of the fully human anti-LAG3 antibodies described herein. In one embodiment, the disease is a cancer, tumor, auto-immune disease, or an infectious disease caused by a virus or pathogenic virus or pathogenic bacteria or pathogenic fungus or pathogenic parasite.

In one embodiment, the anti-LAG3 antibody can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) *Proc. Natl. Acad. Sci. USA* 90:6444-6448; Poljak (1994) *Structure* 2:1121-1123).

In one embodiment, the disease is a cancer which is selected from the group consisting of bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancer, and cancer induced by asbestos.

In one embodiment, the disease is a cancer or tumor which is selected from the group consisting of non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), chronic myeloid leukemia (CIVIL) non-Hodgkin's lymphoma (NHL), acute lymphocytic leukemia (ALL), acute myeloid leukemia (AML), chronic lymphocytic leukemia (CLL), chronic myelogenous leukemia (CML), multiple myeloma (MM), breast cancer, ovarian cancer, head and neck cancer, bladder cancer, melanoma, colorectal cancer, pancreatic cancer, lung cancer, leiomyoma, leiomyosarcoma, glioma, glioblastoma, and solid tumors, wherein solid tumors are selected from the group consisting of breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

In one embodiment, the disease is an auto-immune disease, including Alzheimer's disease, allergy, asthma, celiac disease, Crohn's disease, Grave's disease, inflammatory bowel disease (IBD), lupus, multiple sclerosis, Myasthenia Gravis, polymyalgia rheumatica, rheumatoid arthritis, type I diabetes, or vasculitis.

In one embodiment, the disease is an infectious disease is selected from the group consisting of HIV, Hepatitis (A, B, & C), Influenza, Herpes, *Giardia*, Malaria, *Leishmania*, *Staphylococcus aureus*, *Pseudomonas aeruginosa*, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, and arboviral encephalitis virus.

In one embodiment, the disease is caused by a pathogenic virus including HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

In one embodiment, the disease is cause by a pathogenic bacteria, including chlamydia, rickettsial bacteria, mycobacteria, staphylococci, streptococci, pneumonococci, meningococci and gonococci, klebsiella, proteus, serratia, pseudomonas, legionella, diphtheria, salmonella, bacilli, cholera, tetanus, botulism, anthrax, plague, leptospirosis, or Lyme disease bacteria.

In one embodiment, the disease is caused by a pathogenic fungus, including *Candida* (*albicans, krusei, glabrata, tropicalis*, etc.), *Cryptococcus neoformans, Aspergillus* (*fumigatus, niger*, etc.), *Genus Mucorales* (*mucor, absidia, rhizopus*), *Sporothrix schenkii, Blastomyces dermatitidis, Paracoccidioides brasiliensis, Coccidioides immitis* or *Histoplasma capsulatum*.

In one embodiment, the disease is caused by a pathogenic parasite, including *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii*, or *Nippostrongylus brasiliensis*.

EXAMPLES

The following examples are meant to be illustrative and can be used to further understand embodiments of the present disclosure and should not be construed as limiting the scope of the present teachings in any way.

Example 1

Dose-Dependent Binding to Soluble LAG3 Protein vis ELISA

Figure 3:
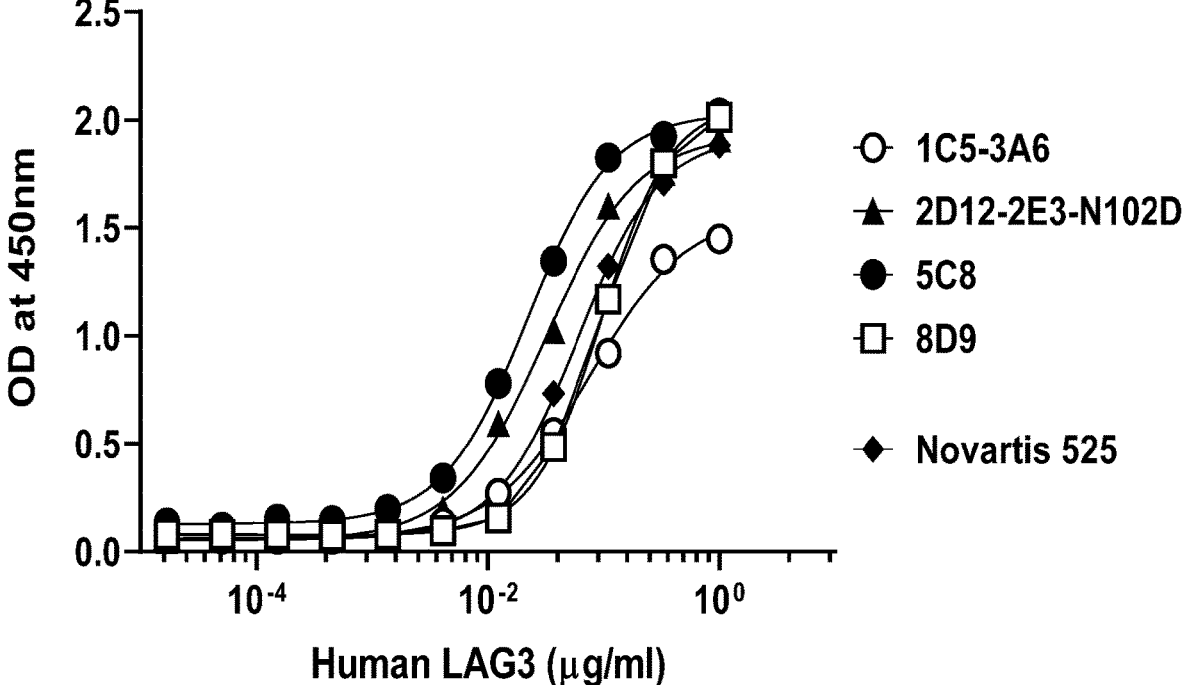
FIG. 3 shows the results of an ELISA assay for dose-dependent binding to soluble human LAG3 antigen. The experiment is described in Example 1.

The Novartis 525 antibody was cloned and produced in-house. Anti-LAG3 antibodies (1C5-3A6, 2D12-2E3-N102D, 5C8 and 8D9) and competitor antibody (Novartis 525) were coated on an Enzyme-Linked Immunosorbent Assay (ELISA) plate at 5 µg/mL (20 µL/well) in 1× Phosphate-Buffered Saline (PBS1×), overnight at 4° C. The plate was washed three times with 250 µL/well of PBS-T (PBS1× supplemented with 0.05 Tween 20). Subsequently, the plate was blocked with 100 µL/well of Blocker Casein in PBS (Thermo Fisher, catalogue No. 37528) for 1 hour at room temperature (RT). After three washings three times with 250 µL/well of PBS-T, the purified human LAG3 His-tag protein (Sino Biological; catalogue No. 16498-H08H) was serially diluted into the wells (top concentration 10 µg/mL; dilution 1:3) and incubated for 1 hour at room temperature. The plate was washed three times with 250 µL/well of PBS-T and binding revealed by applying 50 µL/well of SureBlue™ TMB-1 component microwell peroxidase substrate (SeraCare; catalogue No. 5120-0075). The signal was stopped by using 25 µL/well of 0.16 M sulfuric acid ($H_2SO_4$) stop solution and read on a plate reader at 450 nM. The results are shown in FIG. 3.

Example 2

Measuring Binding Affinities Using Surface Plasmon Resonance (Biacore)

Binding kinetics of anti-LAG3 antibodies (1C5-3A6, 2D12-2E3-N102D, 5C8 and 8D9) and competitor antibody (Novartis 525) were measured using surface plasmon resonance (SPR). Anti-human fragment crystallizable region (Fc region) antibody was immobilized on a CMS sensor chip to approximately 8,000 RU using standard N-hydroxysuccinimide/N-Ethyl-N'-(3-dimethylaminopropyl) carbodiimide hydrochloride (NHS/EDC) coupling methodology. The antibodies (2 µg/mL) were captured for 60 seconds at a flow rate of 10 µL/minute. Recombinant human LAG3-His (Sino Biological; catalogue No. 16498-H08H) was serially diluted in a running buffer of 0.01 M HEPES pH 7.4, 0.15 M NaCl, 3 mM EDTA, 0.05% v/v Surfactant P20 (HBS-EP+). All measurements were conducted in HBS-EP+ buffer with a flow rate of 30 µL/minute. A 1:1 (Langmuir) binding model was used to fit the data. All BIACORE assays were performed at room temperature. The results are shown in FIG. 4. The measured $K_D$ are listed in Table 1 below.

TABLE 1

| measured $K_D$ values | | | | |
|---|---|---|---|---|
| 1C5-3A6 | 5C8 | 2D12-2E3-N102D | 8D9 | Novartis 525 |
| $6.43 \times 10^{-11}$ | $6.15 \times 10^{-12}$ | $8.42 \times 10^{-10}$ | Not measured | $6.16 \times 10^{-12}$ |

Example 3

Cross-Reactivity with Cynomolgus and Mouse LAG3 Antigens

Figure 5:
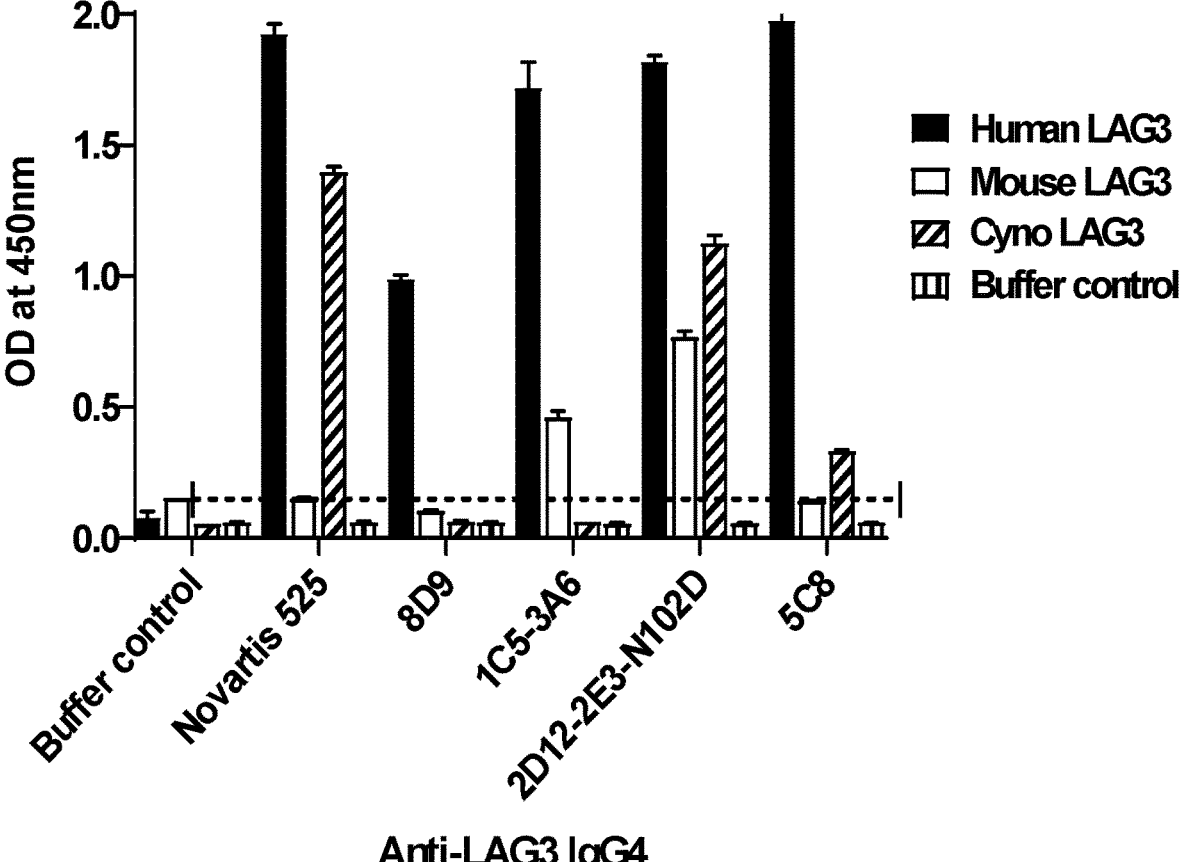
FIG. 5 is a bar graph showing the results of an ELISA assay for various anti-LAG3 antibodies cross reactivity with human, mouse or cynomolgus LAG3 protein. The experiment is described in Example 3.

Human, mouse or cynomolgus LAG3-His Tag recombinant proteins were coated in 50 µL/well of 1× Phosphate-Buffered Saline (PBS1×) on a Ni-NTA ELISA plate (Qiagen, catalogue No. 35061) at 2 µg/mL overnight at 4° C. The plate was washed three times with 250 µL/well of PBS-T (PBS1× supplemented with 0.05% Tween 20). Subsequently, the plate was blocked with 100 µL/well of Blocker Casein in PBS (Thermo Fisher, catalogue No. 37528) for 1 hour at room temperature. After three washings three times with 250 µL/well of PBS-T, the purified antibodies were incubated at 2 µg/mL in PBS-T (50 µL/well) for 1.5 hours at room temperature. The plate was washed three times with 250 µL/well of PBS-T and an HRP-conjugated goat anti-human Fc secondary antibody (Sera Care; catalogue No. 5220-0279) was incubated at dilution 1:5,000 in 50 µL/well for 1 hour at room temperature. Subsequently, the plate was washed three times with 250 µL/well of PBS-T and binding revealed by applying 50 µL/well of SureBlue™ TMB-1 component microwell peroxidase substrate (SeraCare; catalogue No. 5120-0075). The signal was stopped by using 25 µL/well of 0.16 M sulfuric acid ($H_2SO_4$) stop solution and read on a plate reader at 450 nM. The results are shown in FIG. 5.

Example 4

Binding to LAG3-Expressing Cells

The human LAG3/NFAT-Luc reporter Jurkat cell line (BPS Biosciences; catalogue No. 71278) was cultured in complete RPMI (RPMI 1640+10% FCS+Pen/Strep) supplemented with 1 mg/mL G418 and 200 µg/mL Hygromycin B. Wild-type (WT) Jurkat cells were cultured in complete RPMI.

Figure 6:
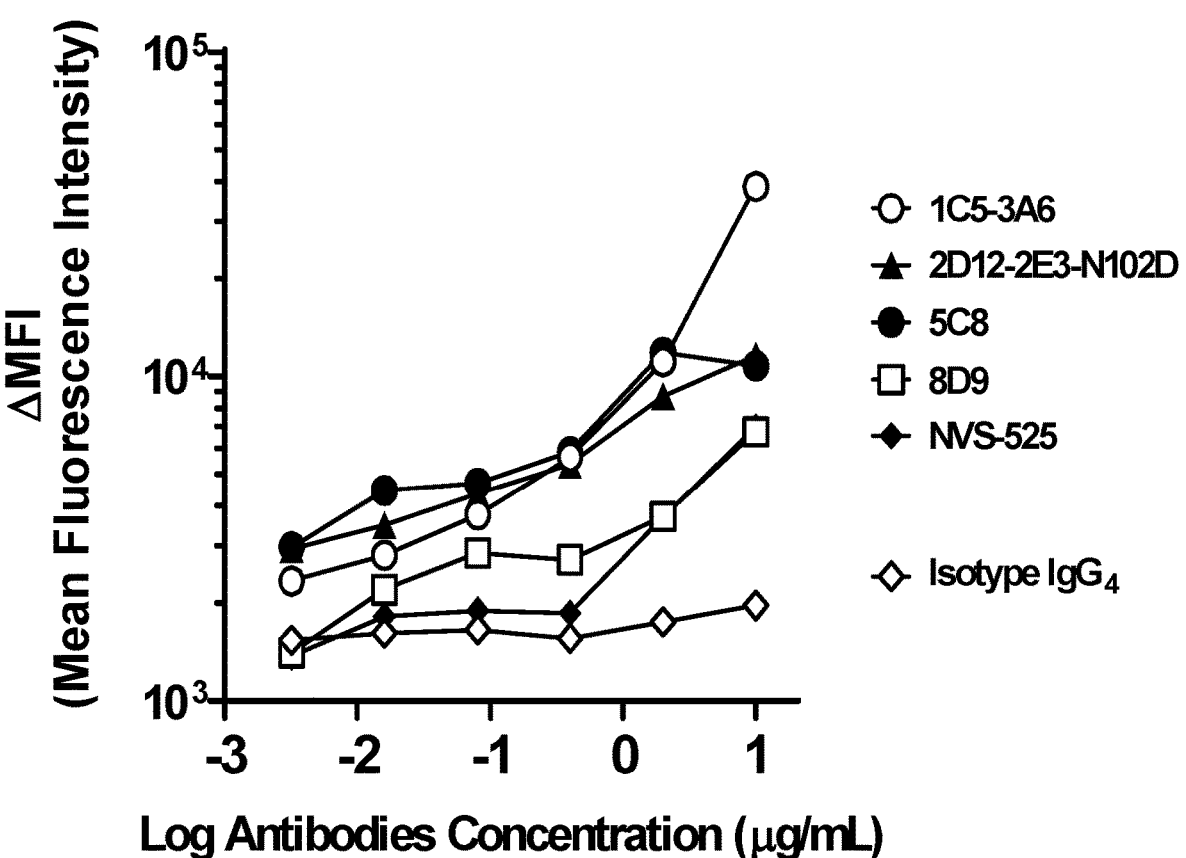
FIG. 6 is a graph comparing the binding capabilities of various anti-LAG3 antibodies to a reporter Jurkat cell line expressing human LAG3/NFAT-Luc. The experiment is described in Example 4.

Cells were plated at 80,000 cells/well in a V-bottom 96-well plate and washed twice using 170 µL/well of FACS buffer (PBS 1×+2% FCS/FBS+0.1% Sodium azide). Anti-LAG3 and isotype control antibodies were diluted in FACS buffer at various concentrations (ranging from 10 to 0.003 µg/mL; dilution 1:5) and incubated with either human LAG3 or WT Jurkat cells in 100 µL/well for 20 min at 4° C. After 2 washes in 170 µL/well of FACS buffer, cells were incubated with 100 µl/well of an AF647-conjugated goat anti-human IgG secondary antibody (Southern Biotech; catalogue no. 2040-31, lot. K471X873C; dilution 1:2,000 in FACS buffer) for 20 min at 4° C. Cells were washed twice, resuspended in 140 µL/well of FACS buffer and acquired by flow cytometry on the Attune NxT. Data were analyzed by using FlowJo v10. ΔMFI was calculated as [(Geo. Mean of LAG3-expressing Jurkat)—(Geo. Mean of WT Jurkat)]. The results are shown in FIG. 6.

Example 5

Specific Binding to SEB-Activated Cynomolgus PBMCs

SEB activation: Fresh cynomolgus monkey peripheral blood mononuclear cells (cyno-PBMCs) were isolated and plated at 2.0E+05 cells/well in a U-bottom plate in 200 µL of complete RPMI (RPMI 1640+10% FCS+Pen/Strep) containing recombinant human IL-2 at 200 U/mL (Miltenyi Biotec; catalogue no. 130-097-748) with or without 300 ng/mL of Staphylococcal Enterotoxin B (SEB) from Toxin Technology, Inc. (catalogue No. 122, lot. 1224171). The cyno-PBMCs were cultured for 4 days in a tissue culture incubator at 37° C., 5% $CO_2$.

Binding assay: On day four, both naïve and activated cyno-PBMCs were washed twice using 170 µL/well of FACS buffer (PBS 1×+2% FCS/FBS+0.1% Sodium azide) and transferred into a V-bottom 96-well plate at 80,000 cells. Anti-LAG3 and isotype control antibodies were diluted in FACS buffer at various concentrations (ranging from 10 to 0.016 µg/mL; dilution 1:5) and incubated with the naïve and activated cyno-PBMCs in 100 µL/well for 20 min at 4° C. After two washes in 170 µL/well of FACS buffer, cells were incubated with 100 µL/well of an AF647-conjugated goat anti-human IgG secondary antibody (Southern Biotech; catalogue no. 2040-31, lot. K471X873C; dilution 1:2,000 in FACS buffer) for 20 min at 4° C. Cells were washed twice, resuspended in 150 µL/well of FACS buffer and acquired by flow cytometry on the Attune NxT. Data were analyzed by using FlowJo v10.

Figure 7A:
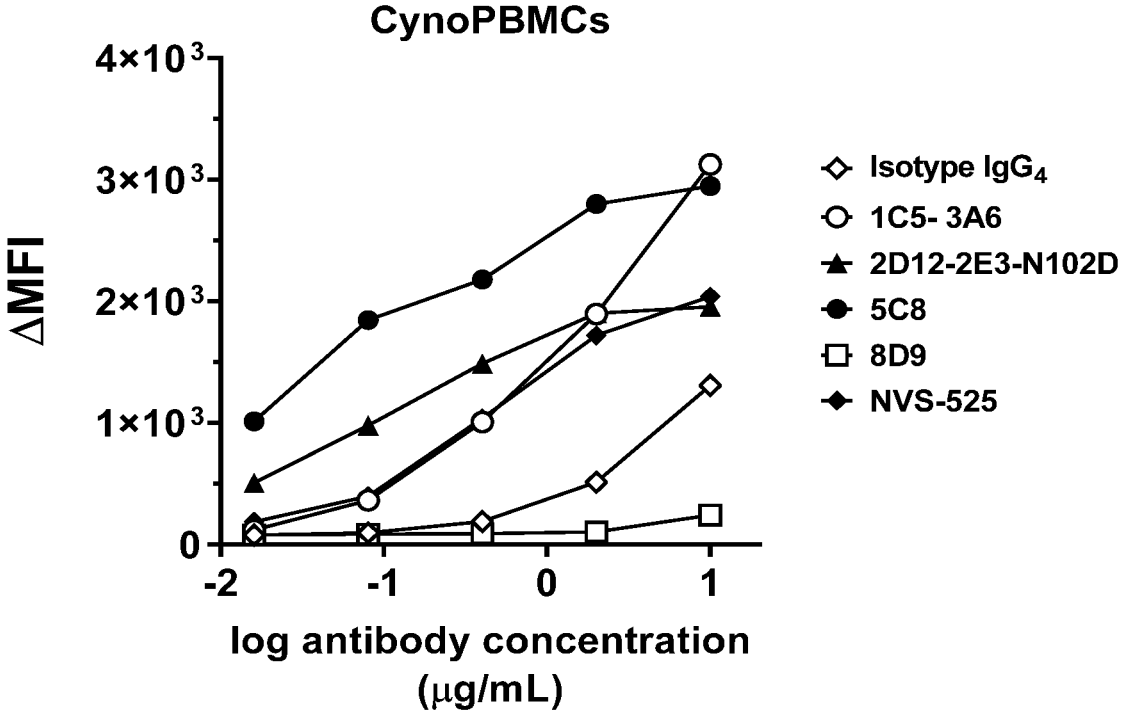
FIG. 7A is a graph comparing the binding capabilities of various anti-LAG3 antibodies to cynomolgus PBMCs activated with Staphylococcal Enterotoxin (SEB). The values along the Y-axis are ΔMFI. The experiment is described in Example 5.

ΔMFI was calculated as [(Geo. Mean of SEB activated cyno-PBMCs)–(Geo. Mean of naïve cyno-PBMCs)]. See FIG. 7A.

Figure 7B:
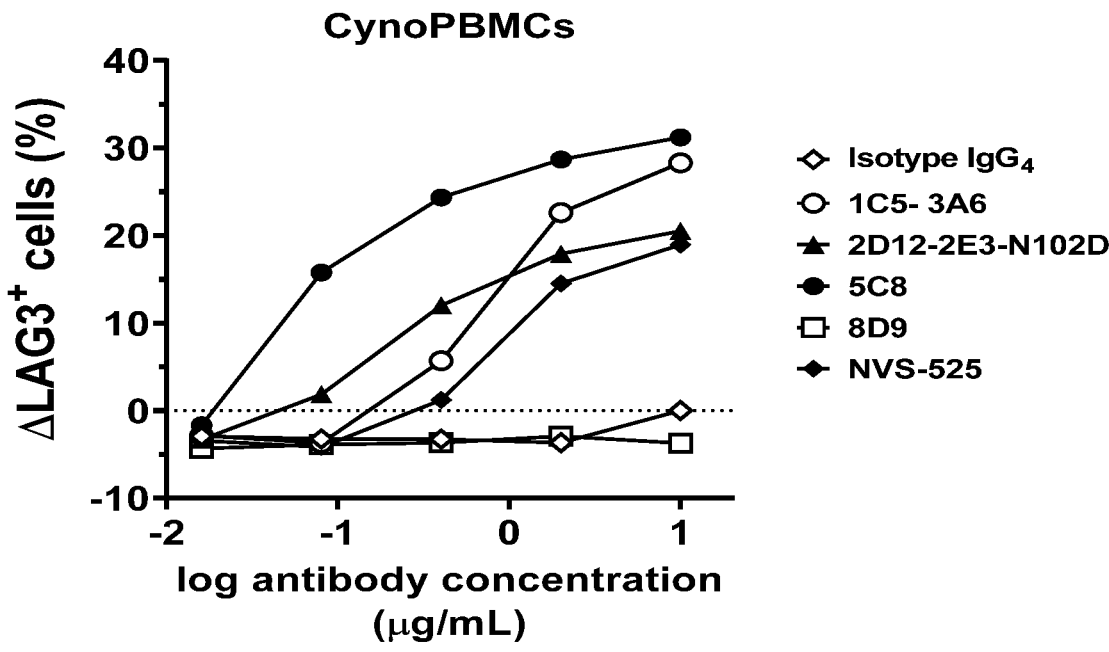
FIG. 7B is a graph comparing the binding capabilities of various anti-LAG3 antibodies to cynomolgus PBMCs activated with Staphylococcal Enterotoxin (SEB), using the same data generated from the experiment described in FIG. 7A. The values along the Y-axis are ΔLAG3+ cells. The experiment is described in Example 5.

ΔLAG3$^+$ Cells was calculated as [(% LAG3$^+$ cells of SEB activated cyno-PBMCs)–(% LAG3$^+$ cells of naïve cyno-PBMCs)]. See FIG. 7B.

Example 6

Detecting Functional Activity of Anti-LAG3 Antibodies in a Reporter Assay

Assay Principal: When Raji and LAG3/NFAT reporter Jurkat cells are co-cultured in presence of superantigen (e.g., Staphylococcal Enterotoxin E), the superantigen cross-links the TCR complexes on effector cells (reporter Jurkat) and the MHC class II on target cells (Raji), resulting in TCR activation and NFAT luciferase signal.

LAG3 and MHC class II interaction prevents this cross-linking and inhibits the TCR activation and NFAT luciferase signal.

In presence of anti-LAG-3 antibodies: the interaction between LAG3 and MHC-II is blocked, promotes T cell activation by superantigen and NFAT-luciferase signal on effector cells.

The human LAG3/NFAT-Luc reporter Jurkat cell line (BPS Biosciences; catalogue No. 71278) was cultured in complete RPMI (RPMI 1640+10% FCS+Pen/Strep) supplemented with 1 mg/mL G418 and 200 µg/mL Hygromycin B. RAJI cells (ATCC; catalogue No. CCL-86) were cultured in complete RPMI.

Preparation of LAG3-expressing cells: Human LAG3/NFAT-Luc reporter Jurkat cells (40,000 cells/well) were plated in a 96-well white clear-bottom assay plate (Costar; catalogue no. 3610) in complete RPMI and pre-incubated with 10, 1 or 0.1 µg/mL (final concentration) of anti-LAG3 or isotype control antibodies (final volume 60 µL/well). During pre-incubation, cells were maintained for 30 minutes in a tissue culture incubator at 37° C., 5% $CO_2$.

Preparation of antigen-presenting cells—RAJI cells: RAJI cells were resuspended at 0.75E+06 cells/mL in complete RPMI containing 0.1 ng/mL of Staphylococcal Enterotoxin E (SEE) from Toxin Technology, Inc. (catalogue No. ET404). During pre-incubation, cells were maintained for 30 minutes in a tissue culture incubator at 37° C., 5% $CO_2$.

Assay initiation and reading: SEE-activated RAJI cells were mixed and 40 µL directly transferred in the wells containing pre-incubated human LAG3/NFAT-Luc reporter Jurkat cells (total volume 100 µL/well). The 96-well white clear-bottom assay plate was incubated for 5 to 6 hours in a tissue culture incubator at 37° C., 5% $CO_2$. The luciferase signal was revealed by applying 100 µL/well of ONE-step luciferase assay system (BPS Biosciences; catalogue no. 60690-1). The plate was placed under slow agitation at room temperature for 15 minutes. The signal was measured using a Spark® TECAN reader. Data were analyzed by subtracting the average background luminescence (cell-free control wells) from the luminescence reading of the other wells. The fold induction of NFAT luciferase reporter expression was calculated as [(background-subtracted luminescence of antibody treated well)/(average background-subtracted luminescence of untreated control wells)]. The reporter assay was conducted twice, and the results are shown in FIGS. 8A and B.

Example 7

Epitope Mapping

Purified anti-LAG3 monoclonal antibodies were coated in 50 µL/well of 1× Phosphate-Buffered Saline (PBS1×) on an ELISA Maxisorp™ flat-bottom plate at 5 µg/mL overnight at 4° C. The plate was washed three times with 250 µL/well of PBS-T (PBS1× supplemented with 0.05 Tween 20). Then, the plate was blocked with 100 µL/well of Blocker Casein in PBS (Thermo Fisher, catalogue No. 37528) for 1 hour at room temperature. After three washings three times with 250 µL/well of PBS-T, recombinant human LAG3-Fc Tag protein (Sino Biological; catalogue no. 16498-H05H) was incubated at 2 µg/mL in PBS-T (50 µL/well) for 1.5 hours at room temperature. The plate was washed three times with 250 µL/well of PBS-T and biotinylated anti-LAG3 Novartis 525 antibody clone (NVS525-biotin was cloned, produced and biotinylated in-house) was incubated at 5 µg/mL in PBS-T (50 µL/well) for 1 hour at room temperature. After three washings in PBS-T, a streptavidin-HRP molecule (Thermo Fisher; catalogue No. N100) diluted 1:5,000 in PBS-T and incubated in 50 µL/well for 30 minutes at room temperature and used to detect bound NVS525-biotin. After washing the plate three times with 250 µL/well of PBS-T, the binding revealed by applying 50 µL/well of SureBlue™ TMB-1 component microwell peroxidase substrate (SeraCare; catalogue No. 5120-0075). The signal was stopped by using 25 µL/well of 0.16 M sulfuric acid ($H_2SO_4$) stop solution and read on a plate reader at 450 nM. The results are shown in FIG. 9.

Example 8

Cytokine Release Assay

Fresh PBMCs (from two different donors) were isolated and diluted at 2.0E+06 cells/mL in complete RPMI (RPMI 1640+10% FCS+Pen/Strep) supplemented with recombinant hIL-2 (1,000 U/mL). Cells were plated out at 2.0E+05 cells/well in a in U-bottom plate (100 µL/well). Next, anti-LAG-3 or isotype control antibody clones were diluted at 10, 1 and 0.1 µg/mL (final concentrations) in complete RPMI containing SEB (Staphylococcal Enterotoxin B, List Biological laboratories; catalogue No. 122) at 100 ng/mL final concentration (50 µL of antibody preparation mixed with 50 µL of SEB both at 2× concentration). The plates were placed in a 37° C. incubator for four days. On Day four, the cells and supernatants were transferred to a V-bottom plate and spun down for 1,400 rpm for 5 minutes. Supernatants were transferred to a V-bottom 96 well plate and frozen down at −80° C. until analysis for cytokines content (IFNγ or others pro-inflammatory cytokines).

Cytokine(s) detection: The proinflammatory panel 1 (human) kit from Meso Scale Discovery (MSD) was used (catalogue No. K15049D) by following the manufacturer recommendations. Briefly, assay samples were thawed at room temperature. In the meantime, the cytokine(s) standards were prepared by performing serial dilutions of calibrator 1 using diluent 2 (catalogue No. R51BB-3; lot. M0020102) in Eppendorf™ tubes. Then, assay samples were diluted in 96-well ultralow attachment plates (Corning; catalogue no. 7007; lot. 18219008) using diluent 2 (usually a final dilution ranging from 1:200 to 1:2,000 is necessary to get a high number of samples within the standard curve range).

Then, an MSD 96-well plate was unsealed and washed three times with 300 µl/well of KPL buffer (Sera Care, catalogue No. 5150-0008; lot. 10430811). Each diluted sample and calibrator were transferred onto the MSD plate at 50 µL/well (avoid bubbles) following the plate layout previously prepared. The plate was sealed using an adhesive plate seal (VWR; catalogue No. 60941-120) and incubated for 2 hours at room temperature under slow agitation. The plate was washed three times with 300 µl/well of KPL buffer and a SULFO-Tag detection antibody prepared in diluent 3 (dilution 1:50) was applied at 25 µl/well. The plate was sealed and incubated at room temperature for two hours under slow agitation in the dark. Subsequently, the plate was washed three times with 300 µl/well of KPL buffer. The signal was revealed by adding 150 µl of the 2×read buffer and detected on a MSD instrument (Meso Sector S600; Model 1201). The results are shown in FIGS. 10A and B.

What is claimed:

1. A LAG3-binding protein comprising a heavy chain variable region and a light chain variable region, wherein the heavy chain variable region comprises the CDR1, CDR2, and CDR3 sequences present in SEQ ID NO: 4 and the light chain variable region comprises the CDR1, CDR2, and CDR3 sequences present in SEQ ID NO: 5; or the heavy chain variable region comprises the CDR1, CDR2, and CDR3 sequences present in SEQ ID NO: 6 and the light chain variable region comprises the CDR1, CDR2, and CDR3 sequences present in SEQ ID NO:7; or the heavy chain variable region comprises the CDR1, CDR2, and CDR3 sequences present in SEQ ID NO: 8 and the light chain variable region comprises the CDR1, CDR2, and CDR3 sequences present in SEQ ID NO: 9; or the heavy chain variable region comprises the CDR1, CDR2, and CDR3 sequences present in SEQ ID NO: 10 and the light chain variable region comprises the CDR1, CDR2, and CDR3 sequences present in SEQ ID NO: 11;

wherein the heavy chain region CDR1, CDR2, and CDR3 sequences, and the light chain variable region CDR1, CDR2, and CDR3 sequences are defined according to Kabat, Chothia, or IMGT numbering system, and optionally wherein the LAG3-binding protein is an antibody or an antigen-binding fragment thereof.

2. The LAG3-binding protein of claim 1, wherein the heavy chain variable region and the light chain variable region comprise the sequence of SEQ ID NOS: 4 and 5, SEQ ID NOS: 6 and 7, SEQ ID NOS: 8 and 9, or SEQ ID NOS: 10 and 11, respectively.

3. The LAG3-binding protein of claim 1, which is a fully human anti-LAG3 Fab fragment.

4. The LAG3-binding protein of claim 1, which is a single chain human anti-LAG3 antibody, and optionally wherein the variable domain region from a heavy chain and the variable domain region from a light chain are joined together with a peptide linker.

5. The LAG3-binding protein of claim 4, wherein the heavy chain variable region and the light chain variable region comprise the sequence of SEQ ID NOS: 4 and 5, SEQ ID NOS: 6 and 7, SEQ ID NOS: 8 and 9, or SEQ ID NOS: 10 and 11, respectively.

6. The LAG3-binding protein of claim 1, wherein the LAG3-binding protein binds human LAG3 with a $K_D$ of $10^{-8}$ M or less; or wherein the LAG3-binding protein binds cynomolgus LAG3 with a $K_D$ of $10^{-6}$ M or less.

7. The LAG3-binding protein of claim 1, comprising an IgG4 class antibody.

8. A pharmaceutical composition comprising a pharmaceutically-acceptable excipient and the LAG3-binding protein of claim 1.

9. A kit comprising the LAG3-binding protein of claim 1.

10. A nucleic acid that encodes (a) (i) the heavy chain variable region of the LAG3-binding protein of claim 1, and (ii) the light chain variable region of the LAG3-binding protein of claim 1; or (b) the LAG3-binding protein of claim 1.

11. A vector comprising the nucleic acid of claim 10.

12. A host cell comprising the vector of claim 11, optionally wherein the vector comprises an expression vector, and wherein the host cell expresses the heavy and the light chain variable regions.

13. A method for preparing a LAG3-binding protein, the method comprising: culturing a population of the host cell of claim 12 under conditions suitable for expressing the LAG3-binding protein, and optionally further comprising: recovering from the host cells the expressed LAG3-binding protein.

14. A method of treating a disease associated with LAG3 over-expression in a subject in need thereof, comprising administering the LAG3-binding protein of claim 1 to the subject.

15. The method of claim 14, wherein the disease is bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of fallopian tubes, carcinoma of endometrium, carcinoma of cervix, carcinoma of vagina, carcinoma of vulva, Hodgkin's Disease, non-Hodgkin's lymphoma, cancer of esophagus, cancer of small intestine, cancer of endocrine system, cancer of thyroid gland, cancer of parathyroid gland, cancer of adrenal gland, sarcoma of soft tissue, cancer of urethra, cancer of penis, acute myeloid leukemia, chronic myeloid leukemia, acute lymphoblastic leukemia, chronic lymphocytic leukemia, solid tumors of childhood, lymphocytic lymphoma, cancer of bladder, cancer of kidney or ureter, carcinoma of renal pelvis, neoplasm of central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancer, or a cancer induced by asbestos.

16. The LAG3-binding protein of claim 2, which is a fully human anti-LAG3 Fab fragment.

* * * * *

SEQUENCE LISTING

<160> NUMBER OF SEQ ID NOS: 13

<210> SEQ ID NO 1
<211> LENGTH: 525
<212> TYPE: PRT
<213> ORGANISM: Homo sapiens

<400> SEQUENCE: 1

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
        130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
        210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365
```

```
Cys Glu Val Thr Pro Val Ser Gly Gln Glu Arg Phe Val Trp Ser Ser
    370             375             380
```

```
Leu Asp Thr Pro Ser Gln Arg Ser Phe Ser Gly Pro Trp Leu Glu Ala
385             390             395             400
```

```
Gln Glu Ala Gln Leu Leu Ser Gln Pro Trp Gln Cys Gln Leu Tyr Gln
            405             410             415
```

```
Gly Glu Arg Leu Leu Gly Ala Ala Val Tyr Phe Thr Glu Leu Ser Ser
            420             425             430
```

```
Pro Gly Ala Gln Arg Ser Gly Arg Ala Pro Gly Ala Leu Pro Ala Gly
            435             440             445
```

```
His Leu Leu Leu Phe Leu Ile Leu Gly Val Leu Ser Leu Leu Leu Leu
    450             455             460
```

```
Val Thr Gly Ala Phe Gly Phe His Leu Trp Arg Arg Gln Trp Arg Pro
465             470             475             480
```

```
Arg Arg Phe Ser Ala Leu Glu Gln Gly Ile His Pro Pro Gln Ala Gln
            485             490             495
```

```
Ser Lys Ile Glu Glu Leu Glu Gln Glu Pro Glu Pro Glu Pro Glu Pro
            500             505             510
```

```
Glu Pro Glu Pro Glu Pro Glu Pro Glu Pro Glu Gln Leu
            515             520             525
```

```
<210> SEQ ID NO 2
<211> LENGTH: 532
<212> TYPE: PRT
<213> ORGANISM: Macaca fascicularis
<220> FEATURE:
<221> NAME/KEY: misc_feature
<222> LOCATION: (73)..(73)
<223> OTHER INFORMATION: Xaa can be any naturally occurring amino acid

<400> SEQUENCE: 2
```

```
Met Trp Glu Ala Gln Phe Leu Gly Leu Leu Phe Leu Gln Pro Leu Trp
1               5               10              15
```

```
Val Ala Pro Val Lys Pro Pro Gln Pro Gly Ala Glu Ile Ser Trp Trp
            20              25              30
```

```
Ala Gln Glu Gly Ala Pro Ala Gln Leu Pro Cys Ser Pro Thr Ile Pro
            35              40              45
```

```
Leu Gln Asp Leu Ser Leu Leu Arg Arg Ala Gly Val Thr Trp Gln His
    50              55              60
```

```
Gln Pro Asp Ser Gly Pro Pro Ala Xaa Ala Pro Gly His Pro Pro Val
65              70              75              80
```

```
Pro Gly His Arg Pro Ala Ala Pro Tyr Ser Trp Gly Pro Arg Pro Arg
            85              90              95
```

```
Arg Tyr Thr Val Leu Ser Val Gly Pro Gly Gly Leu Arg Ser Gly Arg
            100             105             110
```

```
Leu Pro Leu Gln Pro Arg Val Gln Leu Asp Glu Arg Gly Arg Gln Arg
            115             120             125
```

```
Gly Asp Phe Ser Leu Trp Leu Arg Pro Ala Arg Arg Ala Asp Ala Gly
    130             135             140
```

```
Glu Tyr Arg Ala Thr Val His Leu Arg Asp Arg Ala Leu Ser Cys Arg
145             150             155             160
```

```
Leu Arg Leu Arg Val Gly Gln Ala Ser Met Thr Ala Ser Pro Pro Gly
            165             170             175
```

```
Ser Leu Arg Thr Ser Asp Trp Val Ile Leu Asn Cys Ser Phe Ser Arg
            180             185             190
```

```
Pro Asp Arg Pro Ala Ser Val His Trp Phe Arg Ser Arg Gly Gln Gly
```

-continued

```
              195                200                205

Arg Val Pro Val Gln Gly Ser Pro His His His Leu Ala Glu Ser Phe
    210                215                220

Leu Phe Leu Pro His Val Gly Pro Met Asp Ser Gly Leu Trp Gly Cys
225                230                235                240

Ile Leu Thr Tyr Arg Asp Gly Phe Asn Val Ser Ile Met Tyr Asn Leu
                245                250                255

Thr Val Leu Gly Leu Glu Pro Ala Thr Pro Leu Thr Val Tyr Ala Gly
                260                265                270

Ala Gly Ser Arg Val Glu Leu Pro Cys Arg Leu Pro Pro Ala Val Gly
                275                280                285

Thr Gln Ser Phe Leu Thr Ala Lys Trp Ala Pro Pro Gly Gly Gly Pro
    290                295                300

Asp Leu Leu Val Ala Gly Asp Asn Gly Asp Phe Thr Leu Arg Leu Glu
305                310                315                320

Asp Val Ser Gln Ala Gln Ala Gly Thr Tyr Ile Cys His Ile Arg Leu
                325                330                335

Gln Gly Gln Gln Leu Asn Ala Thr Val Thr Leu Ala Ile Ile Thr Val
                340                345                350

Thr Pro Lys Ser Phe Gly Ser Pro Gly Ser Leu Gly Lys Leu Leu Cys
                355                360                365

Glu Val Thr Pro Ala Ser Gly Gln Glu His Phe Val Trp Ser Pro Leu
    370                375                380

Asn Thr Pro Ser Gln Arg Ser Phe Ser Gly Pro Trp Leu Glu Ala Gln
385                390                395                400

Glu Ala Gln Leu Leu Ser Gln Pro Trp Gln Cys Gln Leu His Gln Gly
                405                410                415

Glu Arg Leu Leu Gly Ala Ala Val Tyr Phe Thr Glu Leu Ser Ser Pro
                420                425                430

Gly Ala Gln Arg Ser Gly Arg Ala Pro Gly Ala Leu Arg Ala Gly His
                435                440                445

Leu Pro Leu Phe Leu Ile Leu Gly Val Leu Phe Leu Leu Leu Leu Val
    450                455                460

Thr Gly Ala Phe Gly Phe His Leu Trp Arg Arg Gln Trp Arg Pro Arg
465                470                475                480

Arg Phe Ser Ala Leu Glu Gln Gly Ile His Pro Pro Gln Ala Gln Ser
                485                490                495

Lys Ile Glu Glu Leu Glu Gln Glu Pro Glu Leu Glu Pro Glu Pro Glu
                500                505                510

Leu Glu Arg Glu Leu Gly Pro Glu Pro Glu Pro Gly Pro Glu Pro Glu
                515                520                525

Pro Glu Gln Leu
    530
```

<210> SEQ ID NO 3
<211> LENGTH: 521
<212> TYPE: PRT
<213> ORGANISM: Mus musculus

<400> SEQUENCE: 3

```
Met Arg Glu Asp Leu Leu Leu Gly Phe Leu Leu Leu Gly Leu Leu Trp
1               5                10                15

Glu Ala Pro Val Val Ser Ser Gly Pro Gly Lys Glu Leu Pro Val Val
                20                25                30
```

-continued

```
Trp Ala Gln Glu Gly Ala Pro Val His Leu Pro Cys Ser Leu Lys Ser
        35                  40                  45

Pro Asn Leu Asp Pro Asn Phe Leu Arg Arg Gly Gly Val Ile Trp Gln
        50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
                100                 105                 110

His Pro His Val Gln Leu Glu Glu Arg Gly Leu Gln Arg Gly Asp Phe
        115                 120                 125

Ser Leu Trp Leu Arg Pro Ala Leu Arg Thr Asp Ala Gly Glu Tyr His
        130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
                180                 185                 190

Pro Val Ser Val His Trp Phe Gln Gly Gln Asn Arg Val Pro Val Tyr
                195                 200                 205

Asn Ser Pro Arg His Phe Leu Ala Glu Thr Phe Leu Leu Leu Pro Gln
        210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
                260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
        290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
                340                 345                 350

Gly Leu Pro Gly Ser Arg Gly Lys Leu Leu Cys Glu Val Thr Pro Ala
        355                 360                 365

Ser Gly Lys Glu Arg Phe Val Trp Arg Pro Leu Asn Asn Leu Ser Arg
        370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Ser Gly Ala His Ser Ala Arg Arg
                420                 425                 430

Ile Ser Gly Asp Leu Lys Gly Gly His Leu Val Leu Val Leu Ile Leu
        435                 440                 445

Gly Ala Leu Ser Leu Phe Leu Leu Val Ala Gly Ala Phe Gly Phe His
```

```
                450                 455                 460

Trp Trp Arg Lys Gln Leu Leu Leu Arg Arg Phe Ser Ala Leu Glu His
465                 470                 475                 480

Gly Ile Gln Pro Phe Pro Ala Gln Arg Lys Ile Glu Glu Leu Glu Arg
                485                 490                 495

Glu Leu Glu Thr Glu Met Gly Gln Glu Pro Glu Pro Glu Pro Glu Pro
                500                 505                 510

Gln Leu Glu Pro Glu Pro Arg Gln Leu
        515                 520

<210> SEQ ID NO 4
<211> LENGTH: 124
<212> TYPE: PRT
<213> ORGANISM: Artificial sequence
<220> FEATURE:
<223> OTHER INFORMATION: Anti-LAG3 antibody 1C5-3A6:  Heavy chain
      variable region

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
                20                  25                  30

Tyr Ile His Trp Val Arg Gln Ala Pro Gly Gln Gly Leu Glu Trp Val
            35                  40                  45

Gly Trp Ile Asn Pro Asn Ser Gly Gly Thr Asn Tyr Glu Gln Lys Phe
        50                  55                  60

Gln Gly Arg Val Thr Met Thr Trp Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Glu Gly Trp Ser Asn Asp Trp Tyr Val Gly Tyr Tyr Phe Asp
                100                 105                 110

Tyr Trp Gly Gln Gly Thr Leu Val Thr Val Ser Ser
        115                 120

<210> SEQ ID NO 5
<211> LENGTH: 107
<212> TYPE: PRT
<213> ORGANISM: Artificial sequence
<220> FEATURE:
<223> OTHER INFORMATION: Anti-LAG3 antibody 1C5-3A6:  Light chain
      variable region

<400> SEQUENCE: 5

Asp Ile Gln Met Thr Gln Ser Pro Leu Ser Leu Ser Ala Ser Val Gly
1               5                   10                  15

Asp Arg Val Ser Ile Thr Cys Arg Ala Ser Gln Tyr Ile Gly Thr Ser
                20                  25                  30

Leu Asn Trp Tyr Glu Gln Lys Pro Gly Asn Ser Pro Lys Leu Leu Ile
            35                  40                  45

Thr Gly Ala Ser Arg Leu Gln Ser Gly Val Pro Ser Arg Phe Ser Gly
        50                  55                  60

Ser Gly Ser Gly Thr Asp Phe Thr Leu Thr Ile Asn Thr Leu Gln Pro
65                  70                  75                  80

Asp Asp Leu Ala Thr Tyr Tyr Cys His Gln Ser Tyr Asp Asp Pro Pro
                85                  90                  95

Thr Phe Gly Gln Gly Thr Lys Leu Glu Ile Lys
```

```
              100                105
```

<210> SEQ ID NO 6
<211> LENGTH: 124
<212> TYPE: PRT
<213> ORGANISM: Artificial sequence
<220> FEATURE:
<223> OTHER INFORMATION: Anti-LAG3 antibody 2D12-2E3-N102D:  Heavy chain
      variable region

<400> SEQUENCE: 6

```
Glu Val Gln Leu Val Glu Ser Gly Gly Gly Leu Val Gln Pro Gly Arg
1               5                   10                  15

Ser Leu Arg Leu Ser Cys Val Ala Ser Gly Asp Gly Met Ser Asp Tyr
            20                  25                  30

Asp Met His Trp Val Arg Gln Ala Pro Gly Lys Gly Leu Glu Trp Val
        35                  40                  45

Ser Gly Ile Gly Trp Asn Ser Gly Thr Ile Asp Tyr Ala Asp Ser Val
    50                  55                  60

Lys Gly Arg Phe Ile Ile Ser Arg Asp Asn Ala Lys Asn Ser Leu Tyr
65                  70                  75                  80

Leu Gln Met Asn Ser Leu Arg Pro Glu Asp Thr Ala Leu Tyr Tyr Cys
                85                  90                  95

Ala Lys Glu Ile Leu Asp Tyr Ser Trp Met Ser Val Tyr Gly Met Asp
            100                 105                 110

Val Trp Gly Gln Gly Thr Thr Val Thr Val Ser Ser
        115                 120
```

<210> SEQ ID NO 7
<211> LENGTH: 107
<212> TYPE: PRT
<213> ORGANISM: Artificial sequence
<220> FEATURE:
<223> OTHER INFORMATION: Anti-LAG3 antibody 2D12-2E3-N102D:  Light chain
      variable region

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Gly Thr Tyr
            20                  25                  30

Leu Asn Trp Tyr Gln Gln Ser Pro Gly Lys Ala Pro Lys Leu Leu Ile
        35                  40                  45

Tyr Gly Ala Ser Ser Leu His Ser Gly Val Pro Ser Arg Val Ser Gly
    50                  55                  60

Ser Gly Ser Gly Thr Asp Phe Thr Leu Thr Ile Asn Thr Leu Gln Pro
65                  70                  75                  80

Glu Asp Phe Ala Thr Tyr Phe Cys Gln Gln Ser Tyr Asn Thr Pro Pro
                85                  90                  95

Thr Phe Gly Gln Gly Thr Lys Val Glu Ile Lys
            100                 105
```

<210> SEQ ID NO 8
<211> LENGTH: 121
<212> TYPE: PRT
<213> ORGANISM: Artificial sequence
<220> FEATURE:
<223> OTHER INFORMATION: Anti-LAG3 antibody 5C8:  Heavy chain variable
      region

<400> SEQUENCE: 8

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Asp Ser Gly Tyr Asp Phe Glu Asp Trp Phe Asp Pro Trp Gly
            100                 105                 110

Gln Gly Thr Leu Val Thr Val Ser Ser
        115                 120
```

<210> SEQ ID NO 9
<211> LENGTH: 110
<212> TYPE: PRT
<213> ORGANISM: Artificial sequence
<220> FEATURE:
<223> OTHER INFORMATION: Anti-LAG3 antibody 5C8:  Light chain variable
      region

<400> SEQUENCE: 9

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Asn Thr Ala Ser Leu Thr Val Ser Gly Leu Gln
65                  70                  75                  80

Ala Glu Asp Glu Ala Asp Tyr Tyr Cys Ala Ala Trp Asp Asp Ser Leu
                85                  90                  95

Ser Gly Val Val Phe Gly Gly Gly Thr Gln Leu Thr Val Leu
            100                 105                 110
```

<210> SEQ ID NO 10
<211> LENGTH: 123
<212> TYPE: PRT
<213> ORGANISM: Artificial sequence
<220> FEATURE:
<223> OTHER INFORMATION: Anti-LAG3 antibody 8D9:  Heavy chain variable
      region

<400> SEQUENCE: 10

```
Gln Val Gln Leu Val Gln Ser Gly Ala Glu Val Arg Lys Pro Gly Ser
1               5                   10                  15

Ser Val Lys Val Ser Cys Lys Ala Ser Gly Gly Thr Phe Ser Asn Tyr
            20                  25                  30

Ala Phe Ser Trp Val Arg Gln Ala Pro Gly Leu Gly Leu Glu Trp Leu
        35                  40                  45

Gly Ala Ile Ile Pro Glu Phe Asp Thr Ala Asn Tyr Ala Gln Lys Phe
    50                  55                  60
```

```
Lys Asp Arg Val Thr Ile Thr Ala Asp Asp Ser Thr Thr Thr Val Tyr
65                  70                  75                  80

Met Glu Leu Ser Ser Leu Arg Ser Glu Asp Thr Ala Val Tyr Tyr Cys
                85                  90                  95

Ala Ser Gly Met Trp Asp Tyr Tyr Gly Ser Gly Ser Ser Ile Asp Tyr
            100                 105                 110

Trp Gly Gln Gly Thr Leu Val Thr Val Ser Ser
        115                 120
```

<210> SEQ ID NO 11
<211> LENGTH: 110
<212> TYPE: PRT
<213> ORGANISM: Artificial sequence
<220> FEATURE:
<223> OTHER INFORMATION: Anti-LAG3 antibody 8D9:  Light chain variable
      region

<400> SEQUENCE: 11

```
Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asp Ile Gly Arg Asn
                20                  25                  30

Pro Val Asn Trp Tyr His Gln Phe Pro Gly Thr Ala Pro Lys Leu Leu
            35                  40                  45

Ile Phe Ser Asn Ser His Arg Pro Ser Gly Val Pro Asp Arg Phe Ser
        50                  55                  60

Gly Ser Lys Ser Gly Thr Ser Ala Ser Leu Ala Ile Gly Gly Leu Gln
65                  70                  75                  80

Ser Asp Asp Glu Ala Asp Tyr Tyr Cys Ala Ala Trp Ser Asp Ser Leu
                85                  90                  95

Asn Gly Tyr Val Phe Gly Thr Gly Thr Lys Leu Thr Val Leu
            100                 105                 110
```

<210> SEQ ID NO 12
<211> LENGTH: 30
<212> TYPE: PRT
<213> ORGANISM: Artificial sequence
<220> FEATURE:
<223> OTHER INFORMATION: Peptide linker
<220> FEATURE:
<221> NAME/KEY: MISC_FEATURE
<222> LOCATION: (1)..(30)
<223> OTHER INFORMATION: Repeat sequence (GGGGS)N where N is 1-6.

<400> SEQUENCE: 12

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

<210> SEQ ID NO 13
<211> LENGTH: 15
<212> TYPE: PRT
<213> ORGANISM: Artificial sequence
<220> FEATURE:
<223> OTHER INFORMATION: Exemplary peptide linker

<400> SEQUENCE: 13

```
Gly Gly Gly Gly Ser Gly Gly Gly Gly Ser Gly Gly Gly Gly Ser
1               5                   10                  15
```